US009421399B2

(12) United States Patent
Shapiro et al.

(10) Patent No.: US 9,421,399 B2
(45) Date of Patent: *Aug. 23, 2016

(54) MULTI-MODE CONE BEAM CT RADIOTHERAPY SIMULATOR AND TREATMENT MACHINE WITH A FLAT PANEL IMAGER

(71) Applicant: Varian Medical Systems, Inc., Palo Alto, CA (US)

(72) Inventors: Edward G. Shapiro, Menlo Park, CA (US); Edward J. Seppi, Portola Valley, CA (US); John M. Pavkovich, Palo Alto, CA (US); Stanley W. Johnsen, Palo Alto, CA (US); Richard E. Colbeth, Palo Alto, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 131 days.

This patent is subject to a terminal disclaimer.

(21) Appl. No.: 14/486,819

(22) Filed: Sep. 15, 2014

(65) Prior Publication Data

US 2015/0043709 A1    Feb. 12, 2015

Related U.S. Application Data

(63) Continuation of application No. 13/352,222, filed on Jan. 17, 2012, now Pat. No. 8,867,703, which is a continuation of application No. 11/891,505, filed on Aug. 10, 2007, now Pat. No. 8,116,430, which is a continuation of application No. 10/324,227, filed on Dec. 18, 2002, now Pat. No. 7,945,021.

(51) Int. Cl.
*A61N 5/10*     (2006.01)
*A61B 6/03*     (2006.01)
(Continued)

(52) U.S. Cl.
CPC ............ *A61N 5/1049* (2013.01); *A61B 6/032* (2013.01); *A61B 6/0457* (2013.01);
(Continued)

(58) Field of Classification Search
CPC ................ A61N 5/10; A61N 5/1049; A61N 2005/1054; A61N 2005/1061; A61N 5/1048
USPC ..................................... 378/19, 65
See application file for complete search history.

(56) References Cited

U.S. PATENT DOCUMENTS 3,133,227 A    5/1964 Brown et al.
3,144,552 A    8/1964 Schonberg
(Continued)

FOREIGN PATENT DOCUMENTS

AU    746987    2/2000
AU    2002215340    4/2002
(Continued)

OTHER PUBLICATIONS

Petition for Inter Partes Review (IPR2016-00551) filed on Feb. 3, 2016.*

(Continued)

*Primary Examiner* — Allen C. Ho
(74) *Attorney, Agent, or Firm* — Blakely, Sokoloff, Taylor & Zafman LLP (57) ABSTRACT

A multi-mode cone beam computed tomography radiotherapy simulator and treatment machine is disclosed. The radiotherapy simulator and treatment machine both include a rotatable gantry on which is positioned a cone-beam radiation source and a flat panel imager. The flat panel imager captures x-ray image data to generate cone-beam CT volumetric images used to generate a therapy patient position setup and a treatment plan.

27 Claims, 4 Drawing Sheets (51) Int. Cl.
 *A61B 6/00* (2006.01)
 *A61B 6/04* (2006.01)
 *G01T 1/202* (2006.01)
(52) U.S. Cl.
 CPC .......... *A61B 6/4085* (2013.01); *A61B 6/4233* (2013.01); *A61N 5/10* (2013.01); *A61N 5/103* (2013.01); *A61N 5/1031* (2013.01); *A61N 5/1048* (2013.01); *A61N 5/1064* (2013.01); *G01T 1/202* (2013.01); *A61N 2005/1054* (2013.01); *A61N 2005/1061* (2013.01)

(56) References Cited

U.S. PATENT DOCUMENTS

| | | |
|---|---|---|
| 3,193,717 A | 7/1965 | Nunan |
| 3,784,837 A | 1/1974 | Holmstrom |
| 3,906,233 A | 9/1975 | Vogel |
| 3,987,281 A | 10/1976 | Hodes |
| 4,149,247 A | 4/1979 | Pavkovich et al. |
| 4,149,248 A | 4/1979 | Pavkovich |
| 4,208,675 A | 6/1980 | Bajon et al. |
| 4,209,706 A | 6/1980 | Nunan |
| 4,459,485 A | 7/1984 | Span |
| 4,521,808 A | 6/1985 | Ong et al. |
| 4,547,892 A | 10/1985 | Richey et al. |
| 4,593,967 A | 6/1986 | Haugen |
| 4,628,523 A | 12/1986 | Heflin |
| 4,675,731 A | 6/1987 | Takasu et al. |
| 4,679,076 A | 7/1987 | Vikterlof et al. |
| 4,726,046 A | 2/1988 | Nunan |
| 4,741,621 A | 5/1988 | Taft et al. |
| 4,825,393 A | 4/1989 | Nishiya |
| 4,853,777 A | 8/1989 | Hupp |
| 4,868,843 A | 9/1989 | Nunan |
| 4,868,844 A | 9/1989 | Nunan |
| 5,001,344 A | 3/1991 | Kato et al. |
| 5,014,292 A | 5/1991 | Siczek et al. |
| 5,027,818 A | 7/1991 | Bova et al. |
| 5,039,867 A | 8/1991 | Nishihara et al. |
| 5,080,100 A | 1/1992 | Trotel |
| 5,099,505 A | 3/1992 | Seppi et al. |
| 5,117,445 A | 5/1992 | Seppi et al. |
| 5,157,707 A | 10/1992 | Ohlson |
| 5,168,532 A | 12/1992 | Seppi et al. |
| 5,175,754 A * | 12/1992 | Casey .................... A61B 6/035 378/101 |
| 5,207,223 A | 5/1993 | Adler |
| 5,247,555 A | 9/1993 | Moore et al. |
| 5,262,649 A | 11/1993 | Antonuk et al. |
| 5,332,908 A | 7/1994 | Weidlich |
| 5,335,255 A | 8/1994 | Seppi et al. |
| 5,394,452 A | 2/1995 | Swerdloff et al. |
| 5,411,026 A | 5/1995 | Carol |
| 5,427,097 A | 6/1995 | Depp |
| 5,438,991 A | 8/1995 | Yu et al. |
| 5,442,675 A | 8/1995 | Swerdloff et al. |
| 5,471,516 A | 11/1995 | Nunan |
| 5,509,042 A | 4/1996 | Mazess |
| 5,521,957 A | 5/1996 | Hansen |
| 5,537,452 A | 7/1996 | Sheopard et al. |
| 5,661,773 A | 8/1997 | Swerdloff et al. |
| 5,663,995 A | 9/1997 | Hu |
| 5,673,300 A | 9/1997 | Reckwerdt et al. |
| 5,675,625 A | 10/1997 | Rockseisen |
| 5,692,507 A | 12/1997 | Seppi et al. |
| 5,719,914 A | 2/1998 | Rand et al. |
| 5,724,400 A | 3/1998 | Swerdloff et al. |
| 5,727,554 A | 3/1998 | Kalend et al. |
| 5,748,700 A | 5/1998 | Shepherd et al. |
| 5,751,781 A | 5/1998 | Brown et al. |
| 5,802,136 A | 9/1998 | Carol |
| 5,818,902 A | 10/1998 | Yu |
| 5,835,558 A | 11/1998 | Maschke |
| 5,848,126 A | 12/1998 | Fujita et al. |
| 5,877,501 A | 3/1999 | Ivan et al. |
| 5,912,943 A | 6/1999 | Deucher et al. |
| 5,926,521 A | 7/1999 | Tam |
| 5,929,449 A | 7/1999 | Huang |
| 5,949,811 A | 9/1999 | Baba et al. |
| 5,956,382 A | 9/1999 | Wiener-Avnear et al. |
| 5,960,055 A | 9/1999 | Samarasekera et al. |
| 5,999,587 A | 12/1999 | Ning et al. |
| 6,031,888 A | 2/2000 | Ivan et al. |
| 6,041,097 A | 3/2000 | Roos et al. |
| 6,075,836 A | 6/2000 | Ning |
| 6,078,638 A | 6/2000 | Sauer et al. |
| 6,104,778 A | 8/2000 | Murad |
| 6,104,780 A | 8/2000 | Hanover et al. |
| 6,113,264 A | 9/2000 | Watanabe |
| 6,144,875 A | 11/2000 | Schweikard et al. |
| 6,148,058 A | 11/2000 | Dobbs |
| 6,152,598 A | 11/2000 | Tomisaki et al. |
| 6,198,957 B1 * | 3/2001 | Green .................... A61N 5/1042 378/65 |
| 6,200,024 B1 | 3/2001 | Negrelli |
| 6,219,403 B1 | 4/2001 | Mishihara |
| 6,222,901 B1 | 4/2001 | Meulenbrugge et al. |
| 6,256,366 B1 | 7/2001 | Lai |
| 6,269,141 B1 | 7/2001 | Proksa et al. |
| 6,269,143 B1 | 7/2001 | Tachibana |
| 6,285,739 B1 | 9/2001 | Rudin et al. |
| 6,288,398 B1 | 9/2001 | Stark |
| 6,292,526 B1 | 9/2001 | Patch |
| 6,307,914 B1 | 10/2001 | Kunieda et al. |
| 6,318,892 B1 | 11/2001 | Suzuki et al. |
| 6,325,537 B1 | 12/2001 | Watanabe |
| 6,325,758 B1 | 12/2001 | Carol et al. |
| 6,345,114 B1 | 2/2002 | Mackie et al. |
| 6,370,421 B1 | 4/2002 | Williams et al. |
| 6,381,302 B1 | 4/2002 | Berestov |
| 6,385,286 B1 | 5/2002 | Fitchard et al. |
| 6,385,288 B1 | 5/2002 | Kanematsu |
| 6,429,578 B1 | 8/2002 | Danielson et al. |
| 6,435,715 B1 | 8/2002 | Betz et al. |
| 6,438,202 B1 | 8/2002 | Olivera et al. |
| 6,445,766 B1 | 9/2002 | Whitham |
| 6,449,336 B2 * | 9/2002 | Kim .................... A61N 5/1084 378/65 |
| 6,463,122 B1 | 10/2002 | Moore |
| 6,480,565 B1 | 11/2002 | Ning |
| 6,504,158 B2 * | 1/2003 | Possin ............... H01L 27/14603 250/370.01 |
| 6,507,026 B2 * | 1/2003 | Ikeda ................ H01L 27/14658 250/370.09 |
| 6,508,586 B2 | 1/2003 | Oota |
| 6,560,311 B1 | 5/2003 | Shepard et al. |
| 6,582,121 B2 | 6/2003 | Crain et al. |
| 6,590,953 B2 | 7/2003 | Suzuki et al. |
| 6,661,870 B2 | 12/2003 | Kapatoes et al. |
| 6,661,872 B2 | 12/2003 | Bova |
| 6,714,620 B2 | 3/2004 | Caflisch et al. |
| 6,741,674 B2 | 5/2004 | Lee |
| 6,744,848 B2 | 6/2004 | Stanton et al. |
| 6,800,858 B1 * | 10/2004 | Seppi .................... G01T 1/2018 250/370.01 |
| 6,813,336 B1 | 11/2004 | Siochi |
| 6,842,502 B2 | 1/2005 | Jaffray et al. |
| 6,852,974 B2 * | 2/2005 | Kochi .................... H01J 37/26 250/307 |
| 6,865,254 B2 | 3/2005 | Nafstadius |
| 6,888,919 B2 | 5/2005 | Graf |
| 6,914,959 B2 | 7/2005 | Bailey et al. |
| 6,934,653 B2 | 8/2005 | Ritt |
| 6,968,035 B2 | 11/2005 | Siochi |
| 6,987,831 B2 * | 1/2006 | Ning .................... A61B 6/032 378/20 |
| 6,990,175 B2 | 1/2006 | Nakashima et al. |
| 7,096,055 B1 | 8/2006 | Schweikard |
| 7,221,733 B1 | 5/2007 | Takai et al. |
| 7,227,925 B1 * | 6/2007 | Mansfield ............ A61N 5/1049 378/41 |
| 7,263,165 B2 * | 8/2007 | Ghelmansarai ...... A61N 5/1049 250/370.09 |
| 7,346,144 B2 | 3/2008 | Hughes et al. |

(56) References Cited

U.S. PATENT DOCUMENTS

| | | | |
|---|---|---|---|
| 7,438,685 B2 | 10/2008 | Burdette et al. | |
| 7,453,976 B1* | 11/2008 | Yin | A61B 6/032 378/65 |
| 7,471,765 B2 | 12/2008 | Jaffray et al. | |
| 7,657,304 B2* | 2/2010 | Mansfield | A61B 6/4007 378/197 |
| 7,826,592 B2 | 11/2010 | Jaffray et al. | |
| 7,881,772 B2 | 2/2011 | Ghelmansarai | |
| 7,945,021 B2 | 5/2011 | Shapiro et al. | |
| 8,116,430 B1 | 2/2012 | Shapiro et al. | |
| 8,121,368 B2* | 2/2012 | Wiersma | G06T 7/2046 382/128 |
| 8,788,020 B2* | 7/2014 | Mostafavi | A61B 5/743 324/309 |
| 8,867,703 B2* | 10/2014 | Shapiro | A61B 6/032 378/20 |
| 2001/0001807 A1 | 5/2001 | Green | |
| 2001/0008271 A1 | 7/2001 | Ikeda et al. | |
| 2002/0006182 A1 | 1/2002 | Kim et al. | |
| 2002/0066860 A1 | 6/2002 | Possin | |
| 2002/0179812 A1 | 12/2002 | Kochi et al. | |
| 2003/0007601 A1 | 1/2003 | Jaffray et al. | |
| 2004/0116804 A1 | 6/2004 | Mostafavi | |

FOREIGN PATENT DOCUMENTS

| | | |
|---|---|---|
| DE | 3828639 | 3/1989 |
| DE | 4223488 | 1/1994 |
| DE | 19614643 | 10/1997 |
| DE | 198000946 | 7/1999 |
| DE | 10139934 | 3/2003 |
| EP | 0062941 | 9/1984 |
| EP | 0205720 | 12/1986 |
| EP | 0480035 | 11/1994 |
| EP | 0713677 | 5/1996 |
| EP | 0656797 | 9/1996 |
| EP | 0922943 | 6/1999 |
| EP | 0948930 | 10/1999 |
| EP | 0810006 | 8/2000 |
| EP | 1095628 | 5/2001 |
| EP | 0471455 | 4/2002 |
| EP | 0814869 | 12/2004 |
| EP | 1165182 | 3/2005 |
| EP | 1318857 | 7/2008 |
| EP | 1308185 | 12/2010 |
| EP | 1383427 | 3/2011 |
| EP | 1525902 | 4/2015 |
| EP | 1397700 | 7/2015 |
| FR | 2269745 | 11/1975 |
| FR | 2551664 | 3/1985 |
| GB | 1328033 | 8/1973 |
| JP | 5894835 | 6/1983 |
| JP | 11160440 | 6/1983 |
| JP | 1040069 | 2/1989 |
| JP | H01162682 | 6/1989 |
| JP | 5057028 | 3/1993 |
| JP | 59000076 | 1/1994 |
| JP | 0679006 | 3/1994 |
| JP | H06339541 | 12/1994 |
| JP | 07255717 | 10/1995 |
| JP | 9239044 | 9/1997 |
| JP | 9327453 | 12/1997 |
| JP | 10113400 | 5/1998 |
| JP | 10511595 | 11/1998 |
| JP | 10328318 | 12/1998 |
| JP | 63294839 | 12/1998 |
| JP | 1199148 | 4/1999 |
| JP | 2000116638 | 4/2000 |
| JP | 2000140137 | 5/2000 |
| JP | 2000152927 | 6/2000 |
| JP | 2000317000 | 11/2000 |
| JP | 2001029491 | 2/2001 |
| JP | 2001120528 | 5/2001 |
| JP | 2001095793 | 10/2001 |
| JP | 2004097646 | 4/2004 |
| JP | 2004166975 | 6/2004 |
| JP | 2004194697 | 7/2004 |
| WO | WO-8503212 | 8/1985 |
| WO | WO-9014129 | 11/1990 |
| WO | WO-9106876 | 5/1991 |
| WO | WO-9200567 | 1/1992 |
| WO | WO-9202277 | 2/1992 |
| WO | WO-9220202 | 11/1992 |
| WO | WO-9500204 | 1/1995 |
| WO | WO-9713552 | 4/1997 |
| WO | WO-9742522 | 11/1997 |
| WO | WO-9852635 | 11/1998 |
| WO | WO-9903397 | 1/1999 |
| WO | WO-01/60236 | 2/2001 |
| WO | WO-0160236 | 8/2001 |
| WO | WO-02/13907 | 2/2002 |
| WO | WO-0213907 | 2/2002 |
| WO | WO-02061680 | 8/2002 |
| WO | WO-03008986 | 1/2003 |

OTHER PUBLICATIONS

Petition for Inter Partes Review (IPR2016-00380) filed on Dec. 22, 2015.*

Petition for Inter Partes Review (IPR2016-00341) filed on Dec. 15, 2015.*

Petition for Inter Partes Review (IPR 2016-00315) filed on Dec. 11, 2015.*

Corrected Petition for Inter Partes Review (IPR2016-00476) filed on Jan. 27, 2016.*

Petition for Inter Partes Review (IPR2016-00547) filed on Feb. 2, 2016.*

Petition for Inter Partes Review (IPR2016-00317) filed on Dec. 11, 2015.*

Petition for Inter Partes Review (IPR2015-01401) filed on Jun. 15, 2015.*

"Advanced Workstation for Irregular Field Simulation and Image Matching", Copyright MDS Nordion, (1999), 7 pages.

Andrew, et al., "A video-Based Patient Contou Acquisition System for the Design Radiotherapy Compensators", Abstract, Med Phys, vol. 16 (3), (May-Jun. 1989), 425-430.

Balter, J M., et al., "Daily Targeting of intrahepatic tumors for Radiotherapy", Int. J. Radiation Oncology Biol. Phys., vol. 52, No. 1, (2002), 166-271.

Brewsterfuauf, et al., "Automatic Generation of Beam Apertures", Abstract, Medical Physics, vol. 20, (1993), 1337, 1342.

Cho, P S., et al., "Cone-Beam CT for Radiotherapy Applications", Phys. Med. Biol, vol. 40, (1995), 1863-1883.

Drake, D G., et al., "Characterization of a Fluoroscopic Imaging System for kV and MV Radiography", Med. Phys., vol. 27, No. 5, (May 2000), 898-905.

Elliot, et al., "Interactive Imagine Segmentation for Radiation Treatment Planning", Abstract, IBM Systems Journal, vol. 31, No. 4, (1992), 620-634.

Fahrig, R , et al., "Three-Dimensional COmputed Tomographic Reconstruction Using a C-Arm Mounted XRII: Image Based Correction of Gantry Motion Nonideallities", Med. Phys., vol. 27, No. 1, (Jan. 2000), 30-38.

Feldkamp, L A., et al., "Practical Cone-Beam Algorithm", J. Opt. Soc. Am. A, vol. 1, No. 6, (Jun. 1984), 612-619.

Gademann, et al., "Three-Dimensional Radiation Planning. Studies on Clinical Integration", Abstract, Strahlenther Onkol, vol. 169 (3), (1993), 159-167.

Groh, B A., et al., "A Performance Comparison of Flat-Panel Imager-Based MV and kV Conebeam CT", Med. Phys., vol. 29, No. 6, (Jun. 2002), 967-975.

Hara, et al., "Radiotherapeutic System", 00480035/EP-B1, Citation from World Patent, (1994), 1 page.

Jaffray, et al., SPIE, vol. 3659, (1999), 204-214.

Jaffray, D A., et al., "A Radiographic and Tomographic Imaging System Integrated into a Medical Linear Accelerator for Localization of Bone and Soft-Tissue Targets", Int. J. Radiation Oncology Biol. Phys., vol. 45, No. 3, (1999), 779-789.

(56) References Cited

OTHER PUBLICATIONS

Jaffray, D A., et al., "Cone-Beam Computed Tomography with a Flat-Panel Imager: Initial Performance Characterization", Med, Phys., col. 27, No. 6, (Jun. 2000), 1311-1323.

Jaffray, et al., "Cone-Beam CT: Applications in Image-Guided External Beam Radiotherapy and Brachytherapy", Engineering in medicine and Biology Society, Proceedings of the 22nd Annual International conference of the IEEE, vol. 3, (Jul. 2000), 2044.

Jaffray, et al., "Flat-Paneled Cone-Beam Computed Tomography for Image-Guided Radiation Therapy", Int. J. Radiation Oncology Biol. Phys., vol. 53, No. 5, (2002), 1337-1349.

Keys, D , et al., "A CCTV-Microcomputer Biostereometric System for Use in Radiation Therapy (Topography, Medical Physics, Tissue Compensators)", Abstract, Energy Science and Technology, vol. 45-12B, (1984), 3857.

Kudo, et al., "Feasible Cone Beam Scanning Methods for Exact Reconstruction in Three-Dimensional Tomography", J. Opt. Soc. Am. A., 7, (1990), 2169.

Kuhn, MH , "AIM Project A2003: COmputer Vision in RAdiology (COVIRA)", Abstract, Computer Methods and Programs in Biomedicine, vol. 45, No. 1-2, (Oct. 1994), 17-31.

Kushima, GJ , et al., "New Development of Integrated CT Simulation System for Radiation Therapy Planning", Abstract. Kobe J. Med. Sci., vol. 39, No. 5-6, (Dec. 1993), 17-213.

Kutcher, et al., "Three Dimensional Radiation Treatment Planning", Abstract (1998), Dosimetry in Radiotherapy, vol. 2, Proceedings of an international symposium Held in Vienna, Austria, (Aug.-Sep. 1987).

Masahiro, et al., "Patient Beam Positioning System Using CT Images", Phys. Med. Biol., vol. 27, No. 2, (1982), 301-305.

Midgley, et al., "A Feasability Study for Megavoltage Cone Beam CT Using a Commercial EPID", Phys. Med. Biol. 43, United Kingdom, (1998), 155-169.

Mohan, et al., "Intersection of Shaped Radiation Beams with Arbitrary Image Sections", Abstract, Comput Methods Programs Biomed, vol. 24, (Jun. 1987), 161-168.

Mosleh-Shirazi, M A., et al., "A Cone-Beam Megavoltage CT Scanner for Treatment Certification in Conformal Radiotherapy", Radiotherapy and Oncology, vol. 48, (1998), 319-328.

Nakagawa, K , et al., "Megavoltage CT-Assisted Stereotactic Radiosurgery for Thoracic Tumors: Original Research in the Treatment of Thoracic Neoplasms", Int. J. radiation oncology biol. phys., col. 48, No. 2, (2000), 449-457.

Ning, et al., SPIE, vol. 3659, (1999), 192-203.

Ning, et al., "Flat Panel Detector-Based Cone-Beam Volume CT Angiography lmagrng System Evaluation", EEE Transactions on Medical Imaging, vol. 19, No. 9, Sep. 2000, 949-963.

Ning, et al., "Image Intensifier-Based Volume Tomographic Angiography Imaging System: System Evaluation", SPIE, vol. 2432, (Medical Imaging 1995), 280-290.

Pisani, L , et al., "Setup Error in radiotherapy: On-line Correction using Electronic Kilovoltage and Megavoltage Radiographs", Int. J. Radiation Oncology Biol. Phys., vol. 47, No. 3, (2000), 825-839.

Ragan, "Correction for Distortion in a Beam Outline Transfer Device in Radiotherapy CT-Based Simulation", Med. Phys. 20(1), (Jan./Feb. 1993), 179-185.

Redpath, et al., "Use of a Stimulator and Treatment Planning Computer as a CT Scanner for Radiotherapy Planning", Abstract, Proceedings—Eighth International conference on the Use of Computers in Radiation Therapy held in Toronto, Canada, IEEE, New York, NY, (1984), 281-187.

Reynolds, et al., "An Algorithm for Three-Dimensional Visualization of Radiation Therapy Beams", Abstract, Med Phys, vol. 15 (1), (Jan.-Feb. 1988), 24-28.

Rizo, et al., "Comparison of Two Three-Dimensional X-Ray Cone-Beam-Reconstruction Algorithms with Circular Source Trajectories", J. Opt Soc. Am. A, 10, (1991), 1639.

Ruchala, K J., et al., "Megavoltage CT Tomography System", Phy. Med. Biol., vol. 44, (1999), 2597-2621.

Siewerdsen, et al., Med. Phys. 26, (1999), 2635-2647.

Siewerdsen, et al., Med. Phys. 26, (1999), 1624-1641.

Siewerdsen, J H., et al., "Cone-Beam Computed Tomography with a Flat-Panel Imager: Magnitude and Effect of X-Ray Scatter", Med. Phys., vol. 28, No. 2, (Feb. 2001), 220-231.

Siewerdsen, J H., et al., "Optimization of X-Ray Imaging Geometry (With Specific Application to Flat-Paneled Cone-Beam Computed Tomography)", Med. Phys., vol. 27, No. 8, (Aug. 2000), 1903-1914.

Swindell, W , et al., "Computed Tomography with a Linear Accelerator with Radiotherapy Applications", Med. Phys., vol. 10, No. 4, (Jul./Aug. 1983), 416-420.

Uematsu, M , et al., "A Dual Computed Tomography Linear Accelerator Unit for Stereotactic Radiation Therapy: A New Approach Without Cranially Fixated Stereotactic Frames", Int. J. Radiation Oncology Biol. Phys., vol. 35, No. 3, (1996), 587-592.

Uematsu, M , et al., "Daily Positioning Accuracy of Frameless Stereotactic Radiation Therapy with a Fusion of Computed Tomography and Linear Accelerator (FOCAL) Unit: Evaluation of Z-axis with a Z-marker", Radiotherapy and Oncology, vol. 50, No. 3, (Mar. 1999), 337-339.

Uematsu, M , et al., "Infractional Tumor Position Stability During Computed Tomography (CT)-Guided Frameless Stereotactic Radiation Therapy for Lung or Liver cancers with a Fusion of CT and Linear Accelerator (FOCAL) Unit", Int. J. Radiation Oncology Biol. Phys, vol. 48, No. 2, (2000), 443-448.

Search Report mailed Jan. 21, 2011; EP Appln No. 03786979.9.

Varian Medical Systems, Inc., Communication pursuant to Article 94(3) EPC, EP Application No. 03 786 979.9-1657, dated Jan. 30, 2014, 8 pages.

Yan, et al., "Derivation and Analysis of a Filtered Backprojection Algorithm for Cone Beam Projection", IEEE Trans. Medical Imaging, 10, (1991), 462.

Anderson, R., "Software system for automatic parameter logging on Philips SL20 linear accelerator", Medical & Biological Engineering & Computing, vol. 33, (Mar. 1995), 220-222.

Antonuk, L. E., et al., "A real-time, flat-panel, amorphous silicon, digital x-ray imager", Imaging & Therapeutic Technology, vol. 15, No. 4, (Jul. 1995), 993-1000.

Antonuk, L. E., et al., "Demonstration of megavoltage and diagnostic x-ray imaging with hydrogenated amorphous silicon arrays", Med. Phys., vol. 19, No. 6, (Nov./Dec. 1992), 1455-1466.

Antonuk, L. E., et al., "Thin-film, flat-panel, composite imagers for projection and tomographic imaging", IEEE Transactions on Medical Imaging, vol. 13, No. 3, (Sep. 1994), 482-490.

Biggs, P. J., et al., "A diagnostic x ray field verification device for a 10 mv linear accelerator", Int. J. Radiation Oncology Biol. Phys., vol. 11, No. 3, (Mar. 1985), 635-643.

Boyer, A. L., "Laser cross-hair sidelight", Med. Phys., vol. 5, No. 1, (Jan./Feb. 1978), 58-60.

Chabbal, J., et al., "Amorphous silicon x-ray image sensor", SPIE, vol. 2708, (1996), 499-510.

De Neve, W., et al., "Routine clinical on-line portal imaging followed by immediate field adjustment using a tele-controlled patient couch", Radiotherapy and Oncology, vol. 24, (1992), 45-54.

Ess, A., et al., "Daily monitoring and correction of radiation field placement using a video-based portal imaging system: a pilot study", Int. J. Radiation Oncology Biol. Phys., vol. 22, (1991), 159-165.

Jaffray, D. A., et al., "A Radiographic and Tomographic Imaging System Integrated into a Medical Linear Accelerator for Localization of Bone and Soft-Tissue Targets", Int. J. Radiation Oncology Biol. Phys., vol. 45, No. 3, (1999), 773-789.

Jaffray, D. A., et al., "A volumetric cone-beam CT system based on a 41×41 cm2 flat-panel imager", Proceedings of SPIE, vol. 4320, (2001), 800-807.

Jaffray, D. A., et al., "Cone-beam computed tomography on a medical linear accelerator using a flat-panel imager", XIII, ICCR, Heidelberg, Germany, (2000), 558-560.

Jaffray, D A., et al., "Cone-Beam Computed Tomography with a Flat-Panel Imager: Initial Performance Characterization", Med. Phys., vol. 27, No. 6, (Jun. 2000), 1311-1323.

Jaffray, D. A., et al., "Dual-beam imaging for online verification of radiotherapy field placement", Int. J. Radiation Oncology Biol. Phys., vol. 33, No. 5, (1995), 1273-1280.

(56) References Cited

OTHER PUBLICATIONS

Jaffray, D. A., et al., "Exploring "target of the day" strategies for a medical linear accelerator with cone beam-CT scanning capability", Proceedings of XIIth International Conference on the Use of Computers in Radiation Therapy, Salt Lake City, Utah, (May 27-30, 1997), 172-175.

Jaffray, D. A., et al., "Performance of a volumetric CT scanner based upon a flat-panel imager", SPIE, vol. 3659, (Feb. 1999), 204-214.

Jaffrey, D. A., "Cone-beam ct with a flat-panel imager", File history of U.S. Appl. No. 60/183,590, (Feb. 18, 2000), 48 pages.

Karzmark, C. J., et al., "A primer on theory and operation of linear accelerators in radiation therapy", Bureau of Radiological Health, Rockville, Maryland, (Dec. 1981), 61 pages.

Kirby, M. C., et al., "Clinical applications of composite and realtime megavoltage imaging", Clinical Oncology, vol. 7, (1995), 308-316.

Mackie, T. R., et al., "Tomotherapy: a new concept for the delivery of dynamic conformal radiotherapy", Med. Phys., vol. 20, No. 6, (Nov./Dec. 1993), 1709-1719.

Michalski, J., et al., "Image-guided radiation therapy committee", Int. J. Radiation Oncology Biol. Phys., vol. 51, No. 3, Supplement 2, (2001), 60-65.

Michalski, J. M., et al., "Prospective clinical evaluation of an electronic portal imaging device", Int. J. Radiation Oncology Biol. Phys., vol. 34, No. 4, (1996), 943-951.

Midgley, S. M., et al., "A feasibility study for the use of megavoltage photons and a commercial electronic portal imaging area detector for beam geometry CT scanning to obtain 3D tomographic data sets of radiotherapy patients in the treatment position", 4th International Workshop Electronic Portal Imaging, Amsterdam, (1996), 60-61.

Munro, P., "Portal imaging technology: past, present, and future", Seminars in Radiation Oncology, vol. 5, No. 2, (115-133), Apr. 1995.

Newport Corporation, "AX95 guy pivot support, x95 series structural rails", http://search.newport.com?x2+sku&q2+AX95[Dec. 14, 2015 8:21:55 PM], (1996-2015), 2 pages.

Ning, R., et al., "Flat panel detector-based cone beam Volume CT imaging: detector evaluation", SPIE, vol. 3659, (Feb. 1999), 192-203.

Ning, R., et al., "Selenium flat panel detector-based volume tomographic angiography imaging: phantom studies", SPIE, vol. 3336, (Feb. 1998), 316-324.

Redpath, A. T., "Chapter 6: Simulator computed tomography", The Modern Technology of Radiation Oncology, (1999), 169-187.

Redpath, A. T., "Chapter 13: Megavoltage radiography for treatment verification", The Modern Technology of Radiation Oncology, Medical Physics Publishing, (1999), 481-502.

Scarfe, W. C., et al., "What is cone-beam CT and how does it work?", The Dental Clinics of North America, vol. 52, (2008), 707-730.

Schlegel, W., et al., "The use of computers in radiation therapy", XIIIth International Conference, Heidelberg, Germany, (May 22-25, 2000), 10 pages.

Sephton, R., et al., "A diagnostic-quality electronic portal imaging system", Radiotherapy and Oncology, vol. 35, (1995), 240-247.

Siewerdsen, J. H., et al., "A ghost story: Spatio-temporal response characteristics of an indirect-detection flat-panel imager", Med. Phys., vol. 26, No. 8, (Aug. 1999), 1624-1641.

Siewerdsen, J. H., et al., "Cone-beam computed demography with a flat-panel imager: Effects of image lag", Med. Phys., vol. 26, No. 12, (Dec. 1999), 2635-2647.

Siewerdsen, J. H., et al., "Signal, noise power spectrum, and detective quantum efficiency of indirect-detection flat-panel imagers for diagnostic radiology", Med. Phys., vol. 25, No. 5, (May 1998), 614-628.

SPIE Digital Library, "Medical Imaging 2001: Physics of Medical Imaging", vol. 4320—Proceedings, (Jun. 28, 2001), 10 pages.

Thariat, J., et al., "Past, present, and future of radiotherapy for the benefits of patients", Nat. Rev. Clin. Oncol., vol. 10, (2013), 52-60.

Verellen, D., et al., "A (short) history of image-guided radiotherapy", Radiotherapy and Oncology, vol. 86, (2008), 4-13.

Webb, S., et al., "Tomographic reconstruction from experimentally obtained cone-beam projections", IEEE Transactions on Medical Imaging, vol. MI-6, No. 1, (Mar. 1987), 67-73.

Wong, J., et al., "Initial clinical experience with a gantry mounted dual beam imaging system for setup error localization", I. J. Radiation Oncology Biology Physics; #28—Abstract, vol. 42, No. 1, Supplement, (1998), 1 page.

Xing, L., et al., "Overview of image-guided radiation therapy", Medical Dosimetry, vol. 31, No. 2, (2006), 91-112.

Yan, D., et al., "Adaptive radiation therapy", Phys. Med. Biol., vol. 42, (1997), 123-132.

Yan, D., et al., "The use of adaptive radiation therapy to reduce setup error: a prospective clinical study", Int. J. Radiation Oncology Biol. Phys., vol. 41, No. 3, (1998), 715-720.

Agostinelli, S., et al., "A prototype 3D CT extension for radiotherapy simulators", *Computerized Medical Imaging and Graphics*, vol. 25, (2001), 11-21.

Antonuk, Larry E., "Electronic portal imaging devices: a review and historical perspective of contemporary technologies and research", *Physics in Medicine and Biology*, vol. 47, (Mar. 1, 2002), R31-R65.

Baba, Rika, et al., "Comparison of flat-panel detector and image-intensifier detector for cone-beam CT", *Computerized Medical Imaging and Graphics*, vol. 26, (Jan. 11, 2002), 153-158.

Chin, Lee M., et al., "Dose Optimization with Computer-Controlled Gantry Rotation, Collimator Motion and Dose-Rate Variation", *Int. J. Radiation Oncology Biol. Phys.*, vol. 9, (May 1983), 723-729.

Cho, Paul S., et al., "Digital radiotherapy simulator", *Computerized Medical Imaging and Graphics*, vol. 22, (1998), 1-7.

Cotrutz, C., et al., "Intensity modulated arc therapy (IMAT) with centrally blocked rotational fields", *Phys. Med. Biol.*, vol. 45, (2000), 2185-2206.

Hilbig, Matthias, et al., "Entwicklung eines inversen Bestrahlungsplans mit linearer Optimierung", *Z. Med. Phys.*, vol. 12, (2002), 89-96.

Jaffray, David A., et al., "Flat-panel Cone-beam Computed Tomography for Image-Guided Radiation Therapy", *Int. J. Radiation Oncology Biol. Phys.*, vol. 53, No. 5, (Apr. 3, 2002), 1337-1349.

Jaffray, D.A., et al., "Flat-Panel Cone-Beam CT System on a Mobile Isocentric C-Arm for Image-Guided Brachytherapy", *Medical Imaging 2002: Physics of Medical Imaging*, Proceedings of SPIE vol. 4682, (2002), 209-217.

Klepper, L. Ya., et al., "Methods of mathematical simulation and planning of fractionated irradiation of malignant tumors", *Radiation Physics, Technique and Dosimetry*, (2000).

Lim, Jinho, "Optimization in Radiation Treatment Planning", *A Dissertation Submitted in Partial Fulfillment of the Requirements for the Degree of Doctor of Philosophy*, (2002).

Ma, Ph.D., Lijun, et al., "Optimized Intensity-modulated Arc Therapy for Prostate Cancer Treatment", *Int. J. Cancer (Radiat. Oncol. Invest)*, vol. 96, (2001), 379-384.

Mosleh-Shirazi, Mohammad A., et al., "A cone-beam megavoltage CT scanner for treatment verification in conformal radiotherapy", *Radiotherapy and Oncology*, vol. 48, (Apr. 8, 1998), 319-328

Siewerdsen, J.H., et al., "Cone-beam computed tomography with a flat-panel imager: Effects of image lag", *Med. Phys.*, vol. 26, Issue 12, (Dec. 1999), 2635-2647.

Siewerdsen, Jeffrey A., et al., "Cone-Beam CT with a Flat-Panel Imager: Noise Considerations for Fully 3-D Computed Tomography", *SPIE Physics of Medical Imaging*, vol. 3336, (Feb. 2000), 546-554.

Siewerdsen, Jeffrey H., et al., "Optimization of x-ray imaging geometry (with specific application to flat-panel cone-beam computed tomography)", *Med. Phys.*, vol. 27, Issue 8, (Aug. 2000), 1903-1914.

Tobler, C.M.D., Matt, et al., "The Appication of Dynamic Field Shaping and Dynamic Dose Rate Control in Conformal Rotational Treatment of the Prostate", *Medical Dosimetry*, vol. 27, No. 4, (2002), 251-254.

Wong, Ph.D., Eugene, et al., "Intensity-Modulated Arc Therapy Simplified", *Int. J. Radiation Oncology Biol. Phys.*, vol. 53, No. 1, (2002), 222-235.

(56) References Cited

OTHER PUBLICATIONS

Yan D.Sc., Di , et al., "Adaptive Modification of Treatment Planning to Minimize the Deleterious Effects of Treatment Setup Errors", *Int. J. Oncology Biol. Phys.*, vol. 38, No. 1, (1997), 197-206.
Yu, Cedric X., "Intensity Modulated Arc Therapy: Technology and Clinical Implementation", *Advances in arc therapy*, Sep. 1995, 14 pages.
Yu, Cedric X., "Intensity-modulated arc therapy with dynamic multileaf collimation: an alternative to tomotherapy", *Phys. Med. Biol.*, vol. 40, (1995), 1435-1449.
Yu, D.Sc., Cedric X., et al., "Clinical Implementation of Intensity-Modulated Arc Therapy", *Int. J. Radiation Oncology Biol. Phys.*, vol. 53, No. 2, (2002), 453-463.
"6th International Workshop on Electronic Portal Imaging, EP12K: Program and Abstract Book", (2000), 1-221.
"Digital Imaging and Communications in Medicine (DICOM) Supplement 11 Radiotherapy Objects", (Jun. 4, 1997), 1-103.
Akanuma, A. , et al., "New Patient Set Up in Linac-CT Radiotherapy System—First Mention of a Hybrid CT-Linac System", *IEEE Computer Society*, (1984), 465-467.
Alakuijala, Jyrki , "Algorithms for modeling anatomic and target volumes in image-guided neurosurgery and radiotherapy", (2001), 1-121.
Antonuk, L. , et al., "Initial Performance Evaluation of an Indirect-Detection, Active Matrix Flat-Panel Imager (AMFPI) Prototype for Megavoltage Imaging", *Int. J. Radiation Oncology Bio. Phys.*, vol. 42, No. 2, (1998), 437-452.
Antonuk, L. , et al., "Megavoltage Imaging with a Large-Area, Flat-Panel, Amorphous Silicon Imager", *Int. J. Radiation Oncology Biol. Phys.*, vol. 36, No. 3, (1996), 661-672.
Antonuk, et al., "Signal, noise, and readout considerations in the development of amorphous silicon photodiode arrays for radiotherapy and diagnostic x-ray imaging", *SPIE*, vol. 1443, (1991), 108-119.
Antonuk, L. , et al., "Strategies to improve the signal and noise performance of active matrix, flat-panel imagers for diagnostic x-ray applications", *Medical Physics*, vol. 27, No. 2, (Feb. 2000), 289-306.
Bassett, P. , "An Interactive Computer System for Studying Human Mucociliary Clearance", *Comput. Biol. Med.*, vol. 9, (1979), 97-105.
Berkeshev, O. S., et al., "Practical realization of a method of digital x-ray diagnostics in a scanning-type device", (2001), 36-37.
Bissonnette, J. P., et al., "An Alternative X-Ray Detector for Portal Imaging: High Density Glass Scintillator", (1993), 36-37.
Bissonnette, J. , et al., "Optimal radiographic magnification for portal imaging", *Med. Phys.*, vol. 21, No. 9, (Sep. 1994), 1435-1445.
Bissonnette, J. P., et al., "Physical characterization and optimal magnification of a portal imaging system", *SPIE*, vol. 1651, (1992), 182-188.
Bortfeld, et al., "Clinically relevant intensity modulation optimization using physical criteria", (1997), 1-4.
Boyer, et al., "A review of electronic portal imaging decices (EPIDs)", *Med. Phys.*, vol. 19, No. 1, (1992), 1-16.
Boyer, A. , et al., "Intensity-Modulated Radiotherapy: Current Status and Issues of Interest", *Int. J. Radiation Oncology Bio. Phys.*, vol. 51, No. 4, (2001), 880-914.
Brown, A. , et al., "Three-Dimensional Photon Treatment Planning for Hodgkin's Disease", *Int. J. Radiation Oncology Biol. Phys.*, vol. 21, (May 1992), 205-215.
Budgell, "Temporal resolution requirements for intensity modulated radiation therapy delivered by multileaf collimators", *Phys. Med. Biol.*, 44, (1999), 1581-1596.
Cho, Y. , et al., "Thermal Modelling of a Kilovoltage X-Ray Source for Portal Imaging", *IEEE*, (Jul. 2000), 1856-1860.
Colbeth, R. , et al., "40 × 30 cm Flat Panel Imager for Angiography, R&F, and Cone Beam CT Applications", *Proceedings of SPIE*, vol. 4320, (Feb. 2001), 94-102.
Colbeth, R. , et al., "A Multi-mode X-ray Imager for Medical and Industrial Applications", *IEEE*, (1998), VI-629-VI-632.
Colbeth, R. , et al., "Characterization of a third generation, multi-mode sensor panel", *SPIE*, vol. 3659, (Feb. 1999), 491-500.
Colbeth, R. , et al., "Characterization of an Amorphous Silicon Fluoroscopic Imager", *SPIE*, vol. 3032, (1997), 42-51.
Colbeth, R. , et al., "Flat panel imaging system for fluoroscopy applications", *SPIE*, vol. 3336, (Feb. 1998), 376-387.
Cullity, B. , "Elements of X-Ray Diffraction", Addison-Wesley Publishing Company, Inc. (1978), 6-12 .
Du, M. , et al., "A Multileaf Collimator Field Prescription Preparation System for Conventional Radiotherapy", *Int. J. Radiation Oncology Bio. Phys.*, vol. 30, No. 3, (1994), 707-714.
Du, M. , et al., "A Multileaf Collimator Field Prescription Preparation System for Conventional Radiotherapy", *Int. J. Radiation Oncology Biol. Phys.*, vol. 32, No. 2, (1995), 513-520.
Ebert, M. , et al., "3D image guidance in radiotherapy: a feasibility study", *SPIE*, vol. 4322, (2001), 1807-1816.
El-Mohri, Y. , et al., "Relative dosimetry using active matrix flat-panel imager (AMFPI) technology", *Med. Phys.*, vol. 26, No. 8, (1999), 1530-1541.
Ford, E. C., et al., "Cone-beam CT with megavoltage beams and an amorphous silicon electronic portal imaging device: Potential for verification of radiotherapy of lung", *Medical Physics*, 29, (2002), 2913-2924.
Gilblom, D. , et al., "A real-time, high-resolution camera with an amorphous silicon large-area sensor", *SPIE*, vol. 3302, (1998), 29-38.
Gilblom, D. , et al., "Real-time x-ray imaging with flat panels", *SPIE*, vol. 3399, (1998), 213-223.
Graham, M. , et al., "A Method to Analyze 2-Dimensional Daily Radiotherapy Portal Images from an On- Line Fiber-Optic Imaging System", *Int. J. Radiation Oncology Biol. Phys.*, vol. 20, (1991), 613-619.
Halverson, K. , et al., "Study of Treatment Variation and Neck Tumors Using a Fiber-Optic On-Line Radiotherapy Imaging System", *Int. J. Radiation Oncology Bio. Phys.*, vol. 21, (1991), 1327-1336.
Hartson, M. , et al., "Comparison of CT numbers determined by a simulator CT & a diagnostic scanner", *Nucletron-Oldelft Activity Report*, No. 6, (1995), 37-45.
Herman, M. , et al., "Clinical use of electronic portal imaging: Report of AAPM Radiation Therapy Committee Task Group 58", *Med. Phys.*, vol. 28, No. 5, (2001), 712-737.
Hoogeman, M. S., et al., "A model to simulate day-to-day variations in rectum shape", *int. J. Radiation Oncology Biol. Phys.*, vol. 54, No. 2, (2002), 615-625.
Hunt, P. , et al., "Development of an IMRT quality assurance program using an amorphous silicon electronic portal imaging device", (2000), 1.
I.M.R.T.C.W. Group, "Intensity-Modulated Radiotherapy: Current Status and Issues of Interest", *Int. J. Radiation Oncology Biol. Phys.*, vol. 51, No. 4, (2001), 880-914.
Jaffray, D. , et al., "Activity distribution of a cobalt-60 teletherapy source", *Med. Phys.*, vol. 18, No. 2, (1991), 288-291
Jaffray, D. , et al., "Conebeam Tomograhic Guidance of Radiation Field Placement for Radiotherapy of the Prostate", *International Journal of Radiation Oncology, Biology, and Physics*, (1998), 1-32.
Jaffray, D. , et al., "Flat-panel Cone-beam CT for Image-guided External Beam Radiotherapy", (Oct. 1999), 1-36.
Jaffray, D. , et al., "Image Guided Radiotherapy of the Prostate", *W. Niessen and M. Viergever (Eds)*, (2001), 1075-1080.
Jaffray, D. , et al., "Managing Geometric Uncertainty in Conformal Intensity-Modulated Radiation Therapy", *Seminars in Radiation Oncology*, vol. 9, No. 1, (Jan. 1999), 4-19
Jaffray, D. , et al., "Medical linear accelerator x-ray sources: Variation with make, model, and time", *SPIE*, vol. 1651, (1992), 174-181.
Jaffray, D. , "X-ray scatter in megavoltage transmission radiography: Physical characteristics and influence on image quality", *Med. Phys.*, vol. 21, No. 1, (Jan. 1994), 45-60.

(56) References Cited

OTHER PUBLICATIONS

Jaffray, D., et al., "X-ray sources of medical linear accelerators: Focal and extra-focal radiation", *Medical Physics*, vol. 20, No. 5, (1993), 1417-1427.

Joensuu, Heikki, et al., "Intensiteettimuokattu sädehoito—uusi tekniikka parantanee hoitotuloksia", (2001), 389-394.

Johnsen, S., et al., "Improved Clinac Electron Beam Quality", *Medical Physics*, vol. 10, No. 5, (1983), 737.

Kini, V., et al., "Use of Three-Dimensional Radiation Therapy Planning Tools and Intraoperative Ultrasound to Evaluate High Dose Rate Prostate Brachytherapy", *Int. J. Radiation Oncology Biol. Phys.*, vol. 43, No. 3 (1999), 571-578.

Klausmeier-Brown, M. E., et al., "Real-Time Image Processing in a Flat-Panel, Solid-State, Medical Fluoroscopic Imaging System", *SPIE*, vol. 3303, (Jan. 1998), 2-7.

Korteila, Maria, "Varianin avulla säde tappaa kasvaimen tarkasti", (2000), 1-8.

Kubo, H., "Potential and role of a prototype amorphous silicon array electronic portal imaging device in breathing synchronized radiotherapy", *Med. Phys.*, vol. 26, No. 11, (Nov. 1999), 2410-2414.

Laughlin, J., et al., "Evaluation of High Energy Photon External Beam Treatment Planning: Project Summary", *Int. J. Radiation Oncology Biol. Phys.*, vol. 21, (1991), 3-8.

Lockman, D., et al., "Estimating the dose variation in a volume of interest with explicit consideration of patient geometric variation", *Medical Physics*, vol. 27, No. 9, (Sep. 2000), 2100-2108.

Lof, Johan, "Development of a general framework for optimization of radiation therapy", *Department of Medical Radiation Physics Stockholm 2000*, (2000), 1-140.

Low, et al., "Abutment Region Dosimetry for Serial Tomography", (1999), 193-203.

MacKenzie, M., et al., "Intensity modulated arc deliveries approximated by a large number of fixed gantry position sliding window dynamic multileaf collimator fields", *Medical Physics*, 29, (2002), 2359-2365.

Mallik, R., et al., "Simulator Based CT: 4 Years of Experience at the Royal Norht Shore Hospital, Sydney, Australia", *International Symposium Proceedings*, (Apr. 1993), 177-185.

Martinez, A., et al., "Improvement in Dose Escalation Using the Process of Adaptive Radiotherapy Combined with Three-Dimensional Conformal or Intensity-Modulated Beams for Prostate Cancer", *Int. J. Radiation Oncology Biol. Phys.*, vol. 50, No. 5, (2001), 1226-1234.

Masterson, M., et al., "Interinstitutional Experience in Verification of External Photon Dose Calculations", *Int. J. Radiation Oncology Biol. Phys.*, vol. 21, (1991), 37-58.

Michalski, J., et al., "An Evaluation of Two Methods of Anatomical Alignment of Radiotherapy Portal Images", *Int. J. Radiation Oncology Biol. Phys.*, vol. 27, (1993), 1199-1206.

Michalski, J., et al., "The Use of On-line Image Verification to Estimate the Variation in Radiation Therapy Dose Delivery", *Int. J. Radiation Oncology Biol. Phys.*, vol. 27, (1993), 707-716.

Mosleh-Shirazi, M., "Optimization of the scintillation detector in a combined 3D megavoltage CT scanner and portal imager", *Medical Physics*, 25 (10), (Oct. 1998), 1880-1890.

Mosleh-Shirazi, et al., "Rapid portal imaging with a high-efficiency, large field-of-view detector", (1998), 2333-2346.

Mueller, K., et al., "Cone-Beam Computed Tomography (CT) for a Megavoltage Linear Accelerator (LINAC) Using an Electronic Portal Imaging Device (EPID) and the Algebraic Reconstruction Technique (ART)", *IEEE*, (Jul. 2000), 2875-2878.

Mueller, "Fast and Accurate Three-Dimensional Reconstruction from Cone-Beam Projection Data Using Algebraic Methods", (1998), 1-114.

Muinonen, Simo, "Sadehoiden valmistelun optimointi fysiikan keinoin", (1995), 1-166.

Munro, P., et al., "A Digital Fluoroscopic Imaging Device for Radiotherapy Localization", *Int. J. Radiation Oncology Biol. Phys.*, vol. 18, (1990), 641-649.

Munro, P., et al., "Megavoltage Cone-Beam Computed Tomography Using a High Quantum Efficiency Image Receptor", *Medical Physics*, vol. 29, No. 6, (2002), 1340.

Munro, P., "On Line Portal Imaging", *I. J. Radiation Oncology Biology Physics*, vol. 39, No. 2, (1997), 114.

Munro, P., et al., "Therapy imaging: limitations of imaging with high energy x-ray beams", *SPIE*, vol. 767, (1987), 178-184.

Nag, S., et al., "Intraoperative Planning and Evaluation of Permanent Prostate Brachytherapy: Report of the American Brachytherapy Society", *Int. J. Radiation Oncology Biol. Phys.*, vol. 51, No. 5, (2001), 1422-1430.

Nakagawa, T., et al., "Accuracy improvement of irradiation position and new trend", (2001), 102-105.

Ning, R., et al., "Real Time Flat Panel Detector-Based Volume Tomographic Angiography Imaging: Detector Evaluation", *Proceedings of SPIE*, vol. 3977, (Feb. 2000), 396-407.

Nishiki, M., "X-ray detector in IT era—FPD : Flat Panel Detector", (2001), 1-2.

Partridge, et al., "Linear accelerator output variations and their consequences for megavoltage imaging", *Medical Physics*, 25, (1998), 1443-1452.

Perera, H., et al., "Rapid Two-Dimensional Dose Measurement in Brachytherapy Using Plastic Scintillator Sheet: Liearity, Signal-to-Noise Ratio, and Energy Response Characteristics", *Int. J. Radiation Oncology Biol. Phys.*, vol. 23, (1992), 1059-1069.

Podgorsak, et al., "Dynamic Stereotactic Radiosurgery", *Int. J. Radiation Oncology Biol. Phys.*, vol. 14, (1988), 115-126.

Purdy, J., et al., "State of the Art of High Energy Photon Treatment Planning", *Front. Radiat. Ther. Onc.*, vol. 21, (1987), 4-24.

Rostkowska, J., et al., "Physical and Dosimetric Aspects of Quality Assurance in Sterotactic Radiotherapy", *Rep. Pract. Oncol. Radiother.*, vol. 6, No. 1, (2001), 53-54.

Rowbottom, C., et al., "Simultaneous optimization of beam orientations and beam weights in conformal radiotherapy", *Medical Physics*, 28, (2001), 1696-1702.

Schaller, et al., "Novel Approximate Approach for High-Quality Image Reconstruction in Helical Cone Beam CT at Arbitrary Pitch", (2001), 113-127.

Schewe, J. E., et al., "A room-based diagnostic imaging system for measurement of patient setup", *Medical Physics*, vol. 25, No. 12, (Dec. 1998), 2385-2387.

Seppala, Tiina, "FiR 1 epithermal neutron beam model and dose calculation for treatment planning in neutron capture therapy", (2002), 1-46.

Sharpe, M., et al., "Compensation of x-ray beam penumbra in conformal radiotherapy", *Medical Physics*, vol. 27, No. 8, (Aug. 2000), 1739-1745.

Sharpe, M., et al., "Monitor unit settings for intensity modulated beams delivered using a step- and-shoot approach", *Medical Physics*, vol. 27, No. 12, (Dec. 2000), 2719-2725.

Sidhu, K., et al., "Optimization of Conformal Thoracic Radiotherapy Plance While Using Cone-Beam CT Imaging for Treatment Verification", (2001), 175-176.

Siewerdsen, J., et al., "Empirical and theoretical investigation of the noise performance of indirect detection, active matrix flat-panel imagers (AMFPIs) for diagnostic radiology", *Med. Phys.*, vol. 24, No. 1, (Jan. 1997), 71-89.

Smith, R., et al., "Development of cone beam CT for radiotherapy treatment planning", (2001), S115.

Sontag, M., et al., "State-of-the-Art of External Photon Beam Radiation Treatment Planning", *Int. J. Radiation Oncology Biol. Phys.*, vol. 21, (1991), 9-23.

Studholme, et al., "Automated three-dimensional registration of magnetic resonance and positron emission tomography brain images by multiresolution optimization of voxel similarity measures", *Med. Phys.*, vol. 24, No. 1, (1997), 25-35.

Tepper, J., et al., "Three-Dimensional Display in Planning Radiation Therapy: A Clinical Perspective", *Int. J. Radiation Oncology Biol. Phys.*, vol. 21, (1991), 79-89.

Urie, M., et al., "The Role of Uncertainty Analysis in Treatment Planning", *Int. J. Radiation Oncology Biol. Phys.*, vol. 21, (1991), 91-107.

(56) References Cited

OTHER PUBLICATIONS

Van Herk, M. , et al., "Automatic three-dimensional correlation of CT-CT, CT-MRI, and CT-SPECT using chamfer matching", *Medical Physics*, 21(7), 1163-1178, Jul. 1994.
Varian Medical Systems, "'02 Varian Annual Report", (2002), 1-28.
Vicini, F. , et al., "Dose-Volume Analysis for Quality Assurance of Interstitial Brachytherapy for Breast Cancer", *Int. J. Radiation Oncology Biol. Phys.*, vol. 45, No. 3, (1999), 803-810.
Vicini, F. , et al., "Implementation of 3D-Virtual Brachytherapy in the Management of Breast Cancer: A Description of a New Method of Interstitial Barchytherapy", *Int. J. Radiation Oncology Biol. Phys.*, vol. 40, No. 3, (1998), 629-635.
Vicini, F. , et al., "Low-Dose-Rate Brachytherapy as the Sole Radiation Modality in the Management of Patients with Early-Stage Breast Cancer Treated with Breast-Conserving Therapy: Preliminary Results of a Pilot Trial", *Int. J. Radiation Oncology Biol. Phys.*, vol. 38, No. 2, (1997), 301-310.
Watanabe, Y. , "Development of corn beam X-ray CT system", (Oct. 2002), 778-783.
Weissbluth, M. C., et al., "The Stanford medical linear acclerator. II. Installation and physical measurements", *The Radiological Society of North America*, vol. 72, No. 2, (1959), 242-253
Williamson, J. , et al., "One-dimensional scatter-subtraction method for brachytherapy dose calculation near bounded heterogeneties", *Med. Phys.*, vol. 20, No. 1, (1993), 233-244.
Wong, J. , et al., "A new approach to CT pixel-based photon dose calculations in heterogeneous media", *Medical Physics*, vol. 10, No. 2, (1983), 199-208.
Wong, J. , et al., "Behandlung des Lungenkarzinoms mittels stereotaktischer Strahlentherapie unter Verwednung des weltweit ersten PRIMATOM Systems—eine Fallstudie", (2001), 133-136.
Wong, J. , et al., "Conservative management of osteoradionecrosis", *Oral Medicine Oral Pathology*, vol. 84, No. 1, (Jul. 1997), Oral Surgery.
Wong, J. , et al., "Development of a Second-Generation Fiber-Optic On-Line Image Verification System Effect of small Inhomogeneities on dose in a cobalt-60 beam", *Int. J. Radiation Oncology Biol. Phys.*, vol. 26, (1993), 311-320.
Wong, J. , et al., "Effect of small Inhomogeneities on does in a cobalt-60 beam", *Medical Physics*, vol. 8, No. 6, (1981), 783-791.
Wong, J. , et al., "On methods of inhomogeneity corrections for photon transport", *Medical Physics*, vol. 17, No. 5, (1990), 807-814.
Wong, J. , et al., "On-line image verification in radiation therapy: an early USA experience", *Medical Progress through Technology*, 19, (1993), 43-54.
Wong, J. , et al., "On-line Radiotherapy Imaging with an Array of Fiber-Optic Image Reducers", *Int. J. Radiation Oncology Biol. Phys.*, vol. 18, (1990), 1477-1484.
Wong, J., et al., "Portal Dose Images I: Quantitative Treatment Plan Verification", *Int. J. Radiation Oncology Biol. Phys.*, vol. 18, (1990), 1455-1463.
Wong, J. , et al., "Reconsideration of the power-law (Batho) equation for inhomogeneity corrections", *Med. Phys.*, vol. 9, No. 4, (1982), 521-530.
Wong, J. , et al., "Role of Inhomogeneity Corrections in Three-Dimensional Photon Treatment Planning", *int. J. Radiation Oncology Biol. Phys.*, vol. 21, (1991), 59-69.
Wong, J. , et al., "Second scatter contribution to dose in cobalt-60 beam", *Med. Phys.*, vol. 8, No. 6, (1981), 775-782
Wong, J. , et al., "The Cumulative Verification Image Analysis Tool for Offline Evaluation of Portal Images", *Int. J. Radiation Oncology Biol. Phys.*, vol. 33, No. 5, (1995), 1301-1310.
Wong, J. , et al., "The Use of Active Breathing Control (ABC) to Reduce Martin for Breathing Motion", *Int. J. Radiation oncology Biol. Phys.*, vol. 44, No. 4, (1999), 911-919.
Wong, J , et al., "Treatment Verifications and Patient Dose Estimations Using Portal Dose Imaging", (1988), 213-225.
Woods, R. P., et al., "MRI-PET Registration with Automated Algorithm", *Journal of Computer Assisted Tomography*, 17(4), (Jul. 1993), 536-546.
Wright, M. , et al., "Amorphous silicon dual mode medical imaging system", *SPIE*, vol. 3336, (Feb. 1998), 505-514.
Wu, Y. , et al., "Implementing multiple static field delivery for intensity modulated beams", *Med. Phys.*, vol. 28, No. 11, (Nov. 2001), 2188-2197.
Xing, et al., "Dosimetric verification of a commercial inverse treatment planning system", *Phys. Med. Biol.*, 44, (1999), 463-478.
Xing, et al., "Iterative methods for inverse treatment planning", *Phys. Med. Biol.*, 41, (1996), 2107-2123.
Yan, D. , et al., "A Model to Accumulate Fractionated Dose in a Deforming Organ", *Int. J. Radiation Oncology Biol. Phys.*, vol. 44, No. 3, (1999), 665-675.
Yan, D. , et al., "A New Model for "Accept or Reject" Strategies in Off-Line and On-Line Megavoltage Treatment Evaluation", *Int. J. Radiation Oncology Biol. Phys.*, vol. 31, No. 4, (1995), 943-952.
Yan, D. , et al., "The Influence of Interpatient and Intrapatient Rectum Variation on External Beam Treament of Prostate Cancer", *Int. J. Radiation oncology Biol. Phys.*, vol. 51, No. 4, (2001), 1111-1119.
Ying, X. , et al., "Portal Dose Images II: Patient Dose Estimation", *Int. J. Radiation Oncology Biol. Phys.*, vol. 18, (1990), 1465-1475.
Yu, C. , et al., "A method for implementing dynamic photon beam intensity modulation using independent jaws and a multileaf collimator", *Phys. Med. Biol. 40*, (1995), 769-787.
Yu, C. , et al., "A multiray model for calculating electron pencil beam distribution", *Med. Phys.*, vol. 15, No. 5, (1988), 662-671.
Yu, C. , et al., "Photon does calculation incorporating explicit electron transport", *Med. Phys.*, vol. 22, No. 7, (Jul. 1995), 1157-1166.
Yu, C. , et al., "Photon dose perturbations due to small inhomogeneities", *Med. Phys.*, vol. 1, No. 1, (1987), 78-83.
Zellars, R. C., et al., "Prostate position late in the course of external beam therapy: Patterns and predictors", *Int. J. Radiation Oncology Biol. Phys.*, vol. 47, No. 3, (2000), 655-660.

* cited by examiner

MULTI-MODE CONE BEAM CT RADIOTHERAPY SIMULATOR AND TREATMENT MACHINE WITH A FLAT PANEL IMAGER

CROSS-REFERENCE TO RELATED APPLICATIONS

This application is a continuation of U.S. patent application Ser. No. 13/352,222 filed on Jan. 17, 2012, which is a continuation of U.S. patent application Ser. No. 11/891,505 filed Aug. 10, 2007 issued on Feb. 14, 2012, as U.S. Pat. No. 8,116,430, which is a continuation of U.S. patent application Ser. No. 10/324,227 filed Dec. 18, 2002 and issued as U.S. Pat. No. 7,945,021 on May 17, 2011.

TECHNICAL FIELD

The present invention pertains in general to therapeutic radiology. In particular, the invention involves imaging devices.

BACKGROUND

An objective of radiation therapy is to maximize the amount of radiation to a target volume (e.g., a cancerous tumor) and minimize the amount of radiation to healthy tissues and critical structures. The process of identifying the precise location of the target volume immediately prior to a dose of therapeutic radiation is key to the objective. Since each patient is treated over 30 to 40 fractionated sessions, then the time allowed for each session is relatively short, e.g. 10 to 15 minutes, so the process must be fast as well as accurate.

In the case of electronic portal imaging, megavolt therapeutic X-rays emerging from the patient can be used to generate images. However, this method of target location generates images of low contrast and quality, in addition to incidentally damaging healthy tissue. As a result, imaging with megavoltage (MV) radiation is used primarily for portal verification, that is, to confirm that the treatment volume is being radiated.

Radiotherapy simulator machines have been used to perform the pre-treatment analysis of the target volume before a radiotherapy treatment machine applies the therapeutic radiation. However, traditional radiotherapy simulator machines use bulky image intensifier tube detectors to capture images of the treatment volume. These image intensifier tube detectors have the disadvantage of being very large relative to their imaging area. They also have image spatial distortions from their spherical shaped input surface and the orientation of the intensifier tube with the Earth's magnetic field.

SUMMARY OF AN EMBODIMENT OF THE INVENTION

A multi-mode cone beam computed tomography radiotherapy simulator and treatment machine is disclosed. The radiotherapy simulator and treatment machine both include a rotatable gantry on which is positioned a cone-beam radiation source and a flat panel imager. The flat panel imager captures x-ray image data to generate cone-beam CT volumetric images used to generate a therapy patient position setup and a treatment plan.

BRIEF DESCRIPTION OF THE DRAWINGS

The present invention is illustrated by way of example and not limitation in the figures of the accompanying drawings, in which like references indicate similar elements and in which.

DETAILED DESCRIPTION

In the following description, for purposes of explanation, numerous specific details are set forth in order to provide a thorough understanding of the present invention. It will be evident, however, to one skilled in the art that the present invention may be practiced without these specific details. In some instances, well-known structures and devices are shown in gross form rather than in detail in order to avoid obscuring the present invention. These embodiments are described in sufficient detail to enable those skilled in the art to practice the invention, and it is to be understood that other embodiments may be utilized and that logical, mechanical, electrical, and other changes may be made without departing from the scope of the present invention.

A clinical therapy simulation machine having a cone-beam computed tomograpy (CT) radiation source and a flat-panel imager is described. The clinical therapy simulation machine is capable of manipulating the flat-panel imager and the cone beam CT radiation source to generate x-ray images for determining patient setup/alignment and a clinical treatment plan to be implemented by a clinical treatment machine.

Figure 1:
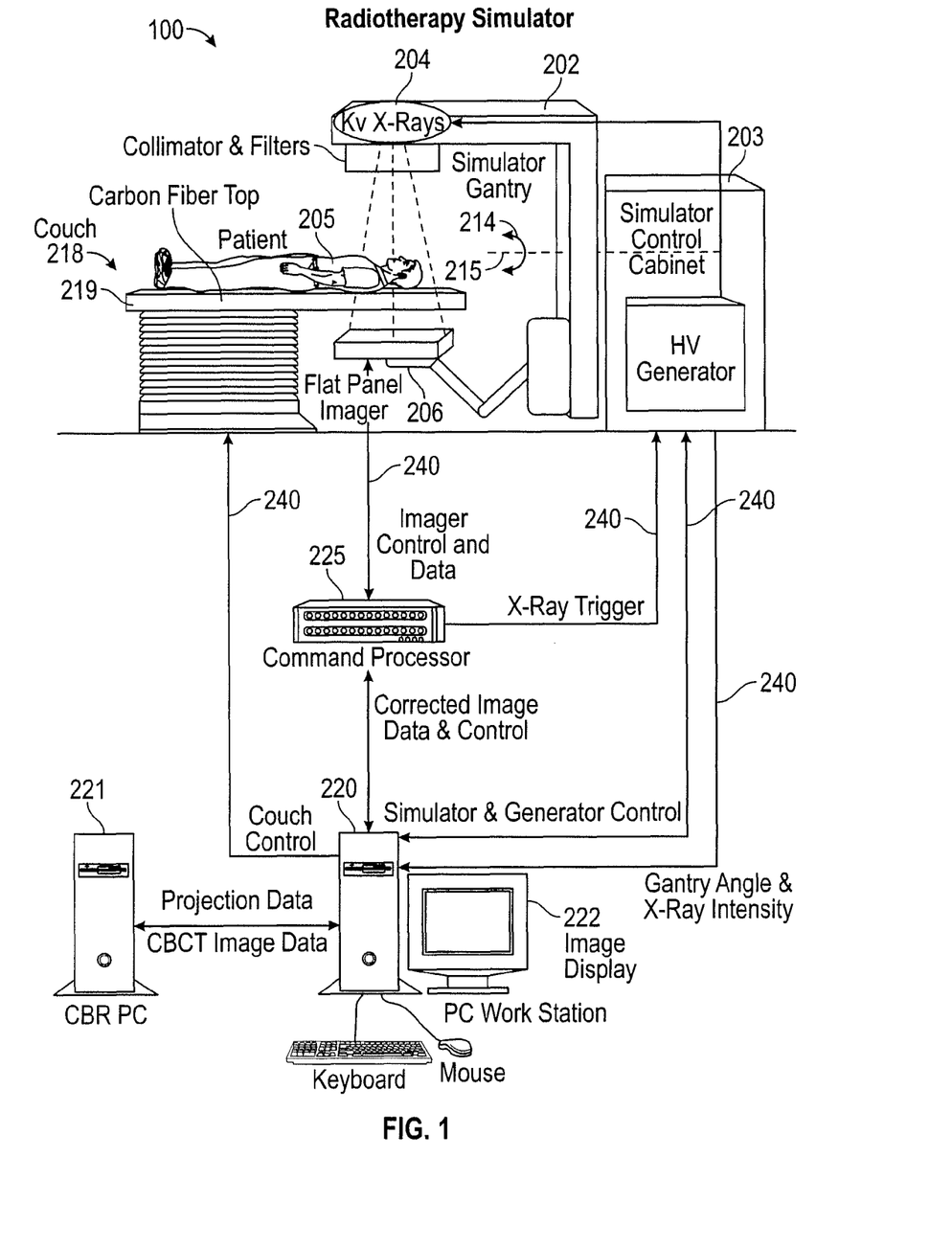
FIG. 1 is an illustration of a side view of one embodiment of a simulation treatment machine.

FIG. 1 is a side view of one embodiment of a simulation treatment machine 100. The simulation treatment machine 100 includes a rotatable gantry 202 pivotably attached to a drive stand 203. A cone-beam CT radiation source 204 and a flat panel imager 206 oppose each other and are coupled to the rotatable gantry 202. In one embodiment, the cone-beam CT radiation source 204 is a kilovoltage radiation source generally in the 50 to 150 kilovolt (kV) energy range, and for example at 125 kilovolts peak (kVp).

A treatment couch 218 is positioned adjacent to the rotatable gantry 202 to place the patient 205 and the target volume within the range of operation for the cone-beam CT radiation source 204 and the flat panel imager 206. The treatment couch 218 may be connected to the rotatable gantry 202 via a communications network and is capable of translating in multiple planes plus angulation (e.g., see 219) for positioning and re-positioning the patient 205 and therefore the target volume.

The rotatable gantry 202 can rotate 214 about an isocenterline 215 to place the cone-beam CT radiation source 204 and flat panel imager 206 at any position 360 degrees around the target volume, for example, to generate CT scan image data. As will be described, cone-beam CT image data can be used to generate a three-dimensional representation of the patient anatomy and the target volume. The image data may further be used to generate a treatment plan to tailor a dose of therapeutic radiation to the target volume.

Figure 2:
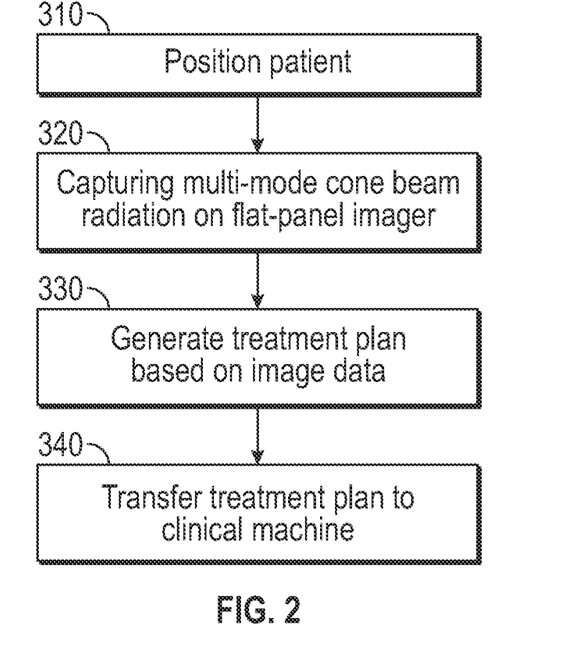
FIG. 2 is an illustration of a process flow of one embodiment of a method for generating a treatment plan.

FIG. 2 is a process diagram of one embodiment of a method for generating a treatment plan. At block 310, a patient 205 is placed on the treatment couch 218 and the treatment couch 218 positioned relative to the simulation treatment machine 100. At block 320, the rotatable gantry 202 rotates around the patient 205 while the radiation from the cone-beam CT radiation source 204 impinges the flat-panel imager 206. The rotatable gantry 202 rotates and collects image data until a computer can calculate a representation of the patient 205 and the target volume. For example, software in a computer may take the image data to generate cone-beam CT volumetric image data for generation of a treatment plan. At block 330, a treatment plan may be generated from the collected image data. The treatment plan may then be transferred, at block 340, to a clinical treatment machine to provide instructions to the clinical treatment machine, for example, to position a therapeutic radiation source to apply a radiation dose to a target volume, and to minimize dose to health tissue and critical structures.

In one embodiment the flat panel imager 206 is a real-time digital x-ray imager incorporating a large-area amorphous silicon sensor array with a high-sensitivity cesium iodide (CsI) scintillator. The flat panel imager 206 may include a receptor module that incorporates the amorphous silicon sensor array, which accepts incoming X-ray photons and converts them to a digital video signal. The X-ray to light conversion may be provided by a thin or thick columnar CsI:Tl (cesium iodide:thallium doped) scintillator The scintillator may be vacuum deposited in a thin (e.g. 0.6 mm) layer or include individual CsI crystals (e.g., being approximately 9 mm thick with an approximate 0.38 mm×0.38 mm pixel pitch) supported in a housing with an aluminum window (e.g., approximately 1 mm thick). The top of the thin CsI scintillator may be coated with a reflective powder/epoxy mixture. Five sides of each thick crystal may be coated with a reflecting powder/epoxy mixture. The sixth side may be in contact with and face the flat-panel sensor. Alternatively, the scintillator components may have other dimensions.

The receptor module may also include a power supply module (e.g., 24 VDC power), interconnecting cables (e.g., fiber optic control and data cables), and drive and readout circuits followed by digital data conversion and transmission capabilities well known to those of ordinary skill in the art.

It should be appreciated that the flat panel imager 206 may be a two-dimensional large flat panel imager that can operate, for example, at 15 to 30 frames per second (fps) over a wide range of dose. In this way, fluoroscopic, radiographic and cone-beam CT imaging can all be achieved with the same flat panel system. Typically, 300-900 projections may be collected during a single rotation of the gantry depending on the image resolution and dose requirements. Fewer projections allow for a faster collection of cone-beam CT image data (e.g., in 20 to 40 seconds depending on gantry speed limits), thereby, allowing for lower dose cone-beam CT images with less patient motion artifacts. Alternatively, the images may operate at other frame rates.

In one embodiment, the flat panel imager 206 has a landscape orientation, an active area of 39.7×29.8 cm$^2$ with 194 micron pixel pitch, and a pixel count of 2048×1536 pixels. It can operate at a frame rate of 7.5 fps in full resolution mode and at a frame rate of 30 fps in 2×2 binned mode—where the pixel count is reduced to 1024×768 pixels$^2$. For example, the flat panel imager 206 may be an amorphous silicon (a-Si) imager available from Varian Medical Systems of Palo Alto, Calif., under the tradename PaxScan™ 4030A. The PaxScan™ 4030A detectors are each 40 cm×30 cm. The detectors may be coupled to signal processing circuitry comprising a preamplifier stage with dynamically controllable signal gain, as described in U.S. Pat. No. 6,486,808, filed on Oct. 16, 2001, assigned to the assignee of the present invention and incorporated by reference, herein, to improve contrast resolution and dynamic range.

The readout electronics may also be located out of the path of the primary cone-beam CT radiation source 204. The flat panel imager 206 may also employ a split data-line where the top half of the array and the bottom half of the array are read out simultaneously. This allows the flat panel imager 206 to read out more rapidly and reduces the parasitic capacitance of the data-lines, which in turn reduces the noise gain of the readout charge amplifiers. It should be appreciated that only half of the frame time is used to read out the pixels. During the rest of the frame time, the flat panel imager 206 can be irradiated without generating any interference patterns due to the pulsing of the cone-beam CT radiation source 204. In addition, it should also be appreciated the control system of the flat panel imager 206 allows an external synchronization signal (from the computer 220) to initiate the readout of a frame. This allows the user to externally control when the flat panel imager 206 will acquire an image.

In one embodiment, a command processor 225 manages the receptor module, processes the digital video, and provides interfaces to other components of the simulator 100. The command processor 225 may include a microcontroller-based, single board computer running a real-time operating system with acquisition, control, and interface software. Also, included in the command processor may be a high-speed digital video interface card, a dedicated image processor card to perform real-time image corrections, a system interface card, and a parallel output to transmit image data to an external image processor and display. Scan-converted digital and analog video may also be provided.

The captured cone-beam CT image projection data may be delivered and stored to a computer 220. As shown in FIG. 1, the computer 220 connects to the simulation treatment machine 100 and the command processor 225 via communications network 240. The computer 220 may control the synchronized movement of the simulator 100 including the rotatable gantry 202, the cone-beam CT radiation source 204, imager 206, and the treatment couch 218. Specifically, the computer 220 may be used by an oncologist to display image projection data on an image display 222, control the intensity of the cone-beam CT radiation source 204, and control the gantry angle.

The cone-beam CT image projection data may also be transferred to a cone-beam CT reconstruction computer 221 that includes software designed to achieve rapid cone-beam CT image generation. The cone-beam CT reconstruction computer 221 can merge or reconstruct the image data into a three-dimensional representation of the patient and target volume. In one embodiment, cone-beam CT reconstruction software may allow for full-cone and partial-cone input data that can produce cone-beam CT images (e.g., approximately 26 to 48 cm diameter) at a specific source-to-imager distance (e.g., 140-150 cm). In addition, in this way, the clinical simulator machine 100 and cone-beam reconstruction software may also allow for large diameter (e.g., approximately 48 cm) axial image volumes.

In one embodiment, the cone-beam CT reconstruction software may transform the image projection data into volumetric CT image data. The volumetric CT image data may include full-fan and/or partial cone image data to reconstruct head size (e.g. 26 cm diameter×17 cm length) and body size (e.g. 48 cm diameter×15 cm length) volumes.

For example, the partial-cone method may be used to obtain body size scans when the flat panel imager is not long enough to image the full body in each projection. If the 15 or 17 cm axial section is not wide enough and therefore does not cover sufficient anatomical volume, then multiple scans can be performed. For example, in the two scan case, the patient may be moved axially by 15 or 17 cm couch movements between scans and the reconstructed image volumes may then be merged to provide a 30 to 34 cm axial view.

In one embodiment, prior to reconstruction, the image projection data is preprocessed to account for x-ray beam and detector properties and the system electronic and geometric properties. The algorithm and its implementation is similar to that used in single slice computer tomography in reconstruction of fan beam data obtained with a one-dimensional detector. For partial cone beam reconstruction, the partial cone image projection data is extended to full cone beam image data and then reconstructed using a full cone beam reconstruction algorithm well known to those of ordinarily skill in the art, such as, for example, the Feldkamp cone beam reconstruction technique. It should be understood that the extension of the partial cone beam image data is performed using techniques similar to those used for the extension of partial fan data in well known single slice fan beam computer tomography.

In one embodiment, using the shape and distance data determined from the generated dimensional representation, the target volume may be automatically identified by the computer system 221 and/or by the inspection of an oncologist. The identified target volume may be applied to a radiotherapy planning computer system 220, which creates a treatment plan to be implemented by a clinical treatment machine. The visualization of the data along arbitrary planes, e.g. sagital, coronal, axial, beams eye view, etc., can be displayed to assist the oncologist. To further enhance the visualization, averaging of volume image data perpendicular to the plane of view, i.e. rectangular voxels may be used.

Figure 3:
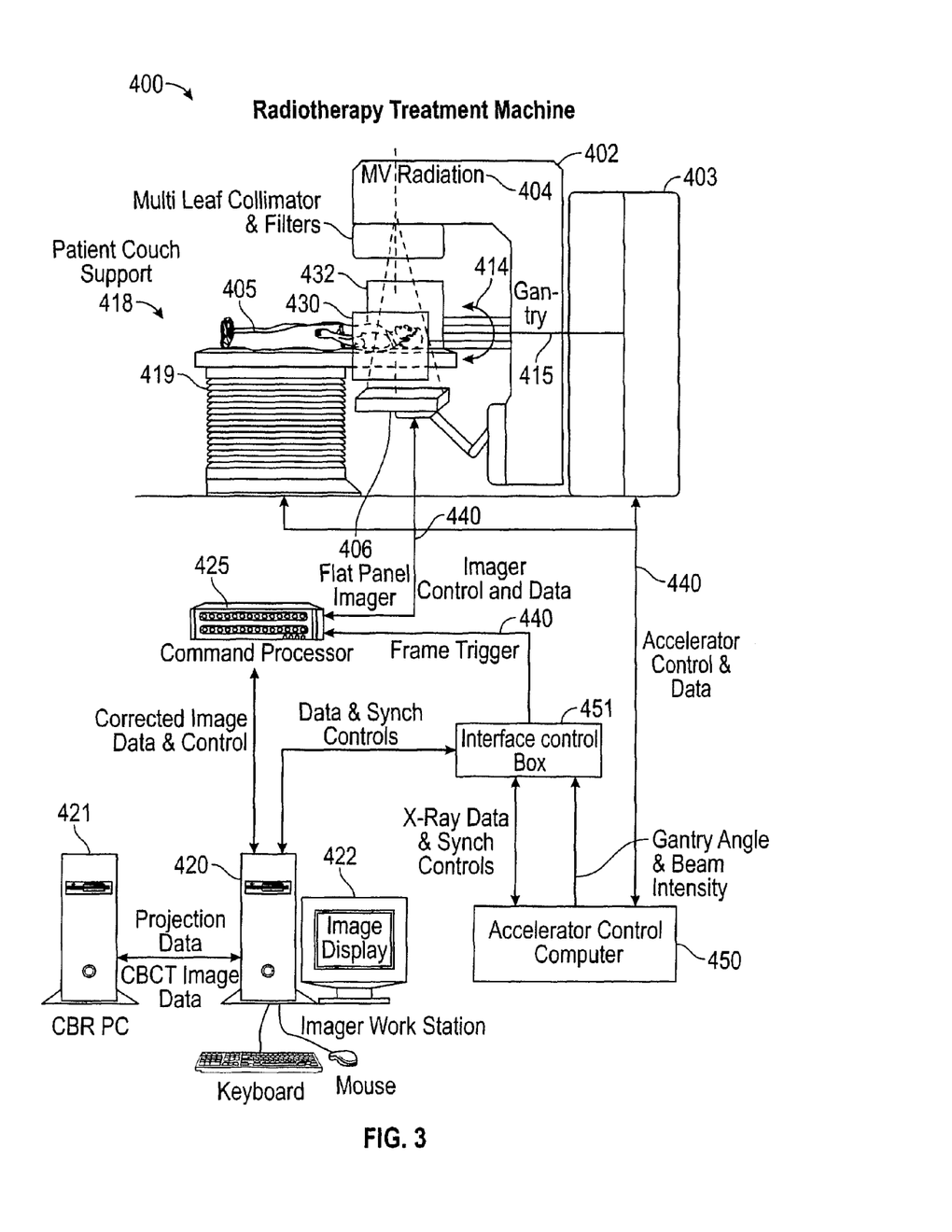
FIG. 3 is a side view of one embodiment of a clinical treatment machine.

FIG. 3 is a side view of one embodiment of a clinical treatment machine 400 that may implement the treatment plan generated by the simulation treatment machine 100 and computer 220. The clinical treatment machine 400 includes a rotatable gantry 402 pivotably attached to a drive stand 403. A cone-beam CT radiation source 404 and a flat panel imager 406 oppose each other and are coupled to the rotatable gantry 402. In one embodiment, the cone-beam CT radiation source 404 is a megavoltage (MV) radiation source generally in the 4 to 25 MV energy range, for example, at 6 MV.

A treatment couch 418 is positioned adjacent to the rotatable gantry 402 to place the patient 405 and the target volume within the range of operation for the cone-beam CT radiation source 404 and the flat panel imager 406. The treatment couch 418 can be capable of translating in multiple planes plus angulation (e.g., see 419) for positioning and re-positioning the patient 405 and therefore the target volume.

The rotatable gantry 402 can rotate 414 about an isocenterline 415 to place the cone-beam CT radiation source 404 and flat panel imager 406 at any position 360 degrees around the target volume. The resulting megavoltage cone-beam CT image data can then be used to tailor a dose of therapeutic radiation based on at least the generated pre-defined treatment plan.

Figure 4:
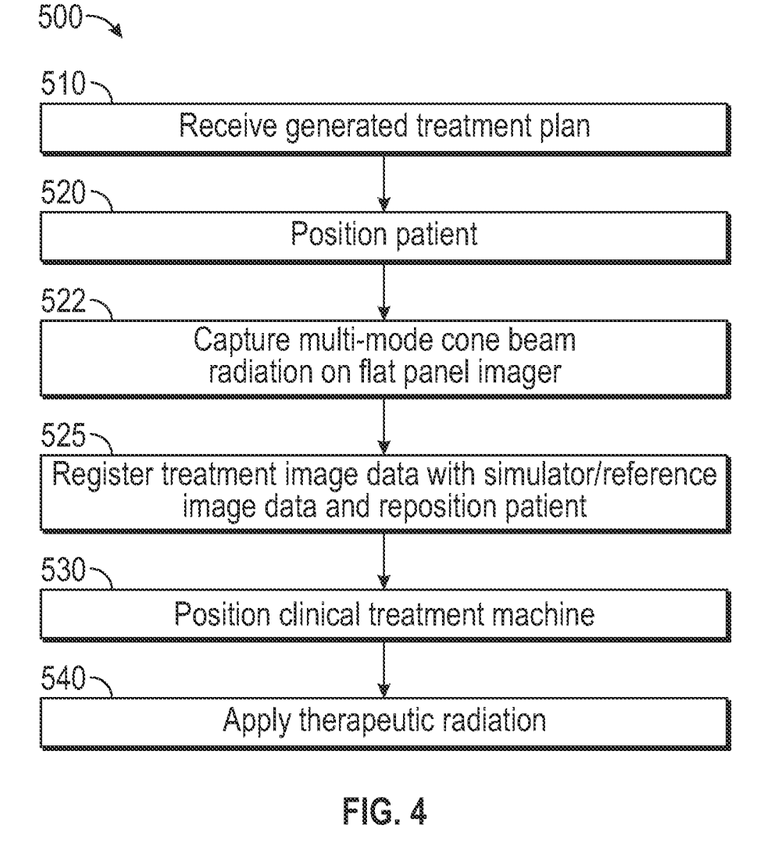
FIG. 4 illustrates a process flow of one embodiment of a method for implementing a treatment plan.

FIG. 4 is a process diagram of one embodiment of a method 500 for implementing a treatment plan. At block 510, an accelerator control computer 450 is provided with the treatment plan generated from the simulation treatment machine 100 for a specific patient 405. For example, the treatment plan may provide initial targeting information about the target volume. At block 520, a patient 405 is placed on the treatment couch 418 and the couch 418 is positioned relative to the clinical treatment machine 400. At block 522, multi-mode cone beam radiation from the cone-beam CT radiation source 404 is captured by the imager 406 to generate images of the target volume. At block 525, the captured image data can be compared/registered with the simulation treatment machine 100 or other reference images to determine the patient repositioning required, if any, before treatment. Image data can also be taken without repositioning to determine the random and systematic errors in treatment position, if any. At block 530, the rotatable gantry 402 is rotated around the patient 405 to a treatment position based on the generated treatment plan. At block 540, a therapeutic radiation dose is applied to the target volume from the cone-beam CT radiation source 404 based on the generated treatment plan. The cone-beam CT radiation source 404 also impinges the flat-panel imager 406 with radiation. In this way, the flat panel imager 406 may provide verification that the target volume is properly targeted. The process 500 may be repeated until the treatment session is complete.

The flat panel imager 406 is similar to the flat panel imager 206 including the corresponding interconnects with a command processor 425, a computer 420, an image display 422, and a cone-beam CT reconstruction computer 421, corresponding with the command processor 225, the computer 220, an image display 222, and the cone-beam CT reconstruction computer 221, as described above. However, in one embodiment, the flat panel imager 406 may have its electronics unfolded from beneath the flat panel imager 406 and the input screen coating may be thicker (e.g., 9 mm vs. 0.6 mm). An example of a flat panel imager that may be used in the present invention is described in U.S. patent Ser. No. 10/013,199, now U.S. Pat. No. 6,800,858 B1, filed on Nov. 2, 2001, assigned to the assignee of the present invention and incorporated herein by reference.

The flat panel imager 406 may also interface with an accelerator interface control box 451. The accelerator interface control box 451 interfaces with an accelerator control computer 450 to provide synchronization and gated control between the flat panel imager 406 and the cone-beam CT radiation source 404 during treatment based on the generated treatment plan. As shown in FIG. 3, interface control box 451, command processor 425, and accelerator control computer 450 connect to clinical treatment machine 400 via communications network 440. This allows single or multiple beam pulse images that are not affected by accelerator noise during readout.

In one embodiment, the accelerator interface control box 451 includes a timing interface. The timing interface coordinates acquisition by the flat panel imager 406 and pulsing of the cone-beam CT radiation source 404. With this interface, as little as one radiation pulse (0.028 cGy at the isocenter) can be used to form projection images.

In one embodiment, the timing interface includes a National Instruments PCI 6602 data acquisition card from National Instruments Corporation of Austin, Tex. USA, that contains hardware and firmware for counting and timing pulses; computer software that provides control logic; and a user interface for the interface system. Alternatively, other cards may also be used.

A master clock signal is derived from a sync signal of the cone-beam CT radiation source 404, which may operate at 360 pulses/s (6 MV) or 180 pulses/s (15-18 MV), according to one embodiment. Using a counter on the National Instruments PCI 6602 card, the sync signal is divided down to produce a master clock signal, and hence are timed relative to the production of cone-beam CT radiation pulses from the cone-beam CT radiation source 404.

The master clock signal may be used to generate two control pulses, one that gates the cone-beam CT radiation source 404 on and off and the other that triggers the flat panel imager 406. In one embodiment, the frequency of these pulses is user selectable, and may be any value below 30 pulses/sec. The relative timing of the two pulses may also be user selectable. When the flat panel imager 406 is triggered there is a period, while the image is being read out (half a frame time) during which no beam from the cone-beam CT radiation source 404 is desired. A user can enter the appropriate delay that will prevent irradiation during the frame readout period of the flat panel imager 406. The length of the gate pulse of the cone-beam CT radiation source 404 is also user selectable. By adjusting the width of the gate pulse, the user can control the number of beam pulses emitted by the cone-beam CT radiation source 404 during each gate pulse.

It should be appreciated that the MV cone-beam CT flat panel imager 406 has a high quantum efficient 9 mm thick CsI:Tl screen (e.g., approximately 10% efficient at 6 MV), which preserves spatial resolution and minimizes dose to the patient by at least a factor of 5 over a standard 1 mm thin copper plate and less than 1 mm GOS (gadolinium oxysulfide) screens used in standard flat panel and screen-camera portal imaging. Therefore, images with as low as one 6 MV accelerator beam pulse (e.g., 0.028 cGy) per frame may be collected. In addition, a low patient dose of 8 to 16 cGy per cone-beam CT data set may be yielded for 300 to 600 CT image frames or projections per data set. The lower dose of the MV cone-beam CT radiation allows for more frequent use on each patient during the typical 30 to 37 fractionated treatment sessions. Moreover, reduced spatial resolution on the MV cone-beam CT scans can be afforded for faster processing time using the cone-beam reconstruction software on the CBR cone-beam CT reconstruction computer 421 to achieve rapid image generation.

It should be appreciated that a separate kV cone-beam CT radiation source (optional and shown as source 430) and another opposing flat panel imager (as described above on the simulator optional and shown as imager 432) may also be coupled to the rotatable gantry 402 to perform a diagnostic cone-beam CT scan. For example, the kV cone-beam CT radiation source 430 and opposing flat panel imager 432 may be coupled to the rotatable gantry 402 at an off axis of e.g. forty-five or ninety degrees from the MV cone-beam CT radiation source 404 and opposing flat panel imager 406. As before, software in the computers 420 and/or 421 may generate the three-dimensional representation of the patient anatomy and target volume from the cone-beam CT image data provided by the kV cone-beam CT radiation source 430. The clinical treatment machine 400 may use the kV cone-beam CT image data to make any necessary adjustments to the treatment plan based on identified movement of the target volume or to determine the amount of patient repositioning required by the treatment couch 418 or collimator movements. In this way, the kV cone-beam CT radiation source 430 and flat panel imager 432 share a common axis of rotation with the MV cone-beam CT radiation source 404 and provide additional information for aligning the patient 405 to the generated simulation treatment plan.

It should also be appreciated that in this way, either the simulation treatment machine 100 and/or the clinical treatment machine 400 diagnostic cone-beam CT image data can be used as a reference for applying the MV radiation beams.

It should also be understood that it is not necessary for the therapeutic radiation to be applied from the exact position(s) where any of the previously generated CT images were taken since the computer software can provide virtual two-dimensional representations for any desired radial location in-between the images.

It should be understood that although the clinical treatment machine 400 has been described as having a cone-beam CT radiation source 404, in alternative embodiments beam shaping, along with intensity modulation, may also be implemented based on the generated treatment plan by directing a therapeutic beam through a dynamic multileaf collimator. The multileaf collimator may include a series of stacked metal shims having a center of shim pairs where each shim of the pairs may be individually moved to create a shaped opening capable of shaping the therapeutic beam. To be effective, the radiation field should be large enough to radiate the entire tumor while at the same time minimize radiating healthy tissue. The collimator may be dynamic in that the shims can rapidly move to reshape the beam, which results in blocking the therapeutic beam from striking certain areas of the target volume based on the treatment plan. Such dynamic shaping may result in different areas of the tumor receiving different amounts of radiation over the time that a radiation dose is applied.

It should be appreciated that more or fewer processes may be incorporated into the methods illustrated in FIGS. 2 and 4 without departing from the scope of the invention and that no particular order is implied by the arrangement of blocks shown and described herein. It further will be appreciated that the method described in conjunction with FIGS. 2 and 4 may be embodied in machine-executable instructions (e.g. software). The instructions can be used to cause a general-purpose or special-purpose processor that is programmed with the instructions to perform the operations described. Alternatively, the operations might be performed by specific hardware components that contain hardwired logic for performing the operations, or by any combination of programmed computer components and custom hardware components. The methods may be provided as a computer program product that may include a machine-readable medium having stored thereon instructions that may be used to program a computer (or other electronic devices) to perform the methods. For the purposes of this specification, the terms "machine-readable medium" shall be taken to include any medium that is capable of storing or encoding a sequence of instructions for execution by the machine and that cause the machine to perform any one of the methodologies of the present invention. The term "machine-readable medium" shall accordingly be taken to included, but not be limited to, solid-state memories, optical and magnetic disks, and carrier wave signals. Furthermore, it is common in the art to speak of software, in one form or another (e.g., program, procedure, process, application, module, logic . . . ), as taking an action or causing a result. Such expressions are merely a shorthand way of saying that execution of the software by a computer causes the processor of the computer to perform an action or produce a result.

It should be appreciated that a clinical simulation machine having a cone-beam radiation source and flat-panel imagers, as described, allows for identification of a target volume via fluoroscopic, radiographic, and cone-beam CT imaging. In this way, the generation of the treatment plan via the clinical simulation machine prior to the application of therapeutic radiation, increases the accuracy of treating the tumor target.

Furthermore, embodiments of the invention as described above may capture images while the gantry is continuously rotating versus traditional systems that stop and shoot every, approximately, four degrees around the patient, thereby further lessening the time for completion.

It should also be appreciated that the cone-beam volumetric reconstruction software can utilize image projection data at non-uniformly spaced gantry angles. Thus the data collection does not require a precise gantry speed of rotation. There is a normalizing detector at the radiation source, which is used to correct for system output variations. In one embodiment, the support arms for the flat panel imagers 206 and 406 are sufficiently precise in mechanical stability during gantry rotation that no compensating spatial corrections are required.

Although the present invention has been described with reference to specific exemplary embodiments, it will be evident that various modifications and changes may be made to these embodiments without departing from the broader scope of the invention as set forth in the claims. Accordingly, the specification and drawings are to be regarded in an illustrative rather than a restrictive sense.

What is claimed is:

1. A method to perform a clinical treatment, comprising:
   receiving a treatment plan at a computer of a radiation treatment machine;
   storing reference image data on said computer;
   positioning a patient at an initial position on a treatment couch of the radiation treatment machine;
   rotating a gantry coupled to a frame of the radiation treatment machine;
   emitting cone-beam radiation from a radiation source coupled to the gantry;
   transmitting at least a portion of the cone-beam radiation through said patient;
   capturing first image projection data using a flat-panel kV imager coupled to the gantry, wherein capturing the first image projection data includes capturing at least a portion of the portion of the cone-beam radiation transmitted through said patient;
   generating cone-beam computed tomography (CT) volumetric image data from the first image projection data;
   registering said cone-beam computed tomography (CT) volumetric image data with said reference image data;
   repositioning the patient based on the cone-beam computed tomography (CT) volumetric image data, wherein repositioning the patient comprises moving said treatment couch prior to beginning the clinical treatment;
   applying therapeutic radiation to a target volume using the treatment plan;
   capturing second image projection data using a flat-panel MV imager coupled to the gantry, wherein capturing the second image projection data includes capturing at least a portion of the therapeutic radiation applied to the target volume; and
   changing the speed of rotation of the gantry during rotation of the gantry.

2. The method of claim 1, wherein capturing the second image projection data includes capturing the second image projection data while changing the speed of rotation of the gantry during a continuous rotation of the gantry about the target volume.

3. A method to perform a clinical treatment, comprising:
   receiving a treatment plan at a computer of a radiation treatment machine;
   storing reference image data on said computer;
   positioning a patient at an initial position on a treatment couch;
   rotating a gantry coupled to a frame of the radiation treatment machine;
   emitting cone-beam radiation from a radiation source coupled to the gantry;
   transmitting at least a portion of the cone-beam radiation through said patient;
   capturing first image projection data using a flat-panel kV imager coupled to the gantry, wherein capturing the first image projection data includes capturing at least a portion of the portion of the cone-beam radiation transmitted through said patient;
   generating cone-beam computed tomography (CT) volumetric image data from the first image projection data;
   registering said cone-beam computed tomography (CT) volumetric image data with reference image data;
   repositioning the patient based on the cone-beam computed tomography (CT) volumetric image data, wherein repositioning the patient comprises moving said treatment couch prior to beginning the clinical treatment;
   applying therapeutic radiation to a target volume using the treatment plan; and
   capturing second image projection data using a flat-panel MV imager coupled to the gantry, wherein capturing the second image projection data includes capturing at least a portion of the therapeutic radiation applied to the target volume at non-uniformly spaced angles with respect to rotation of the gantry.

4. The method of claim 3, wherein capturing the second image projection data includes continuously rotating the gantry about the target volume while capturing the second image projection data at non-uniformly spaced angles with respect to rotation of the gantry.

5. The method of claim 4, wherein capturing the second image projection data at non-uniformly spaced angles with respect to rotation of the gantry comprises predetermining non-uniformly spaced angles with respect to rotation of the gantry.

6. A method to perform a clinical treatment, comprising:
   receiving a treatment plan at a computer of a radiation treatment machine;
   storing reference image data on said computer;
   positioning a patient at an initial position on a treatment couch;
   rotating a gantry coupled to a frame of the radiation treatment machine;
   emitting cone-beam radiation from a radiation source coupled to the gantry;
   transmitting at least a portion of the cone-beam radiation through said patient;
   capturing first image projection data using a flat-panel kV imager coupled to the gantry;
   generating cone-beam computed tomography (CT) volumetric image data from the first image projection data;
   registering said cone-beam computed tomography (CT) volumetric image data with reference image data;
   repositioning the patient based on the cone-beam computed tomography (CT) volumetric image data, wherein repositioning the patient comprises moving said treatment couch prior to beginning the clinical treatment;
   applying therapeutic radiation to a target volume using the treatment plan;
   capturing second image projection data using a flat-panel MV imager coupled to the gantry, wherein capturing the second image projection data includes capturing at least a portion of the therapeutic radiation applied to the target volume at non-uniformly spaced angles with respect to rotation of the gantry; and wherein capturing the second image projection data includes changing the speed of rotation of the gantry during rotation of the gantry.

7. The method of claim 6, wherein capturing the second image projection data includes continuously rotating the gantry about the target volume (1) while capturing the second image projection data at non-uniformly spaced angles with respect to rotation of the gantry, and (2) while changing the speed of rotation of the gantry during rotation of the gantry.

8. The method of claim 7, wherein capturing the second image projection data at non-uniformly spaced angles with respect to rotation of the gantry comprises predetermining non-uniformly spaced angles with respect to rotation of the gantry.

9. A method to perform a clinical treatment, comprising:
receiving a treatment plan at a computer of a radiation treatment machine;
positioning a patient at an initial position on a treatment couch of the radiation treatment machine;
rotating a gantry coupled to a frame of the radiation treatment machine;
emitting cone-beam radiation from a radiation source coupled to the gantry;
transmitting at least a portion of the cone-beam radiation through said patient;
capturing first image projection data using a flat-panel kV imager coupled to the gantry, wherein capturing the first image projection data includes capturing at least a portion of the portion of the cone-beam radiation transmitted through said patient;
generating cone-beam computed tomography (CT) volumetric image data from the first image projection data;
repositioning the patient based on the cone-beam computed tomography (CT) volumetric image data, wherein repositioning the patient comprises moving said treatment couch prior to beginning the clinical treatment;
applying therapeutic radiation to a target volume using the treatment plan;
capturing second image projection data using a flat-panel MV imager coupled to the gantry, wherein capturing the second image projection data includes capturing at least a portion of the therapeutic radiation applied to the target volume; and
changing the speed of rotation of the gantry during rotation of the gantry.

10. The method of claim 9, wherein capturing the second image projection data includes capturing the second image projection data while changing the speed of rotation of the gantry during a continuous rotation of the gantry about the target volume.

11. A method to perform a clinical treatment, comprising:
receiving a treatment plan at a computer of a radiation treatment machine;
positioning a patient at an initial position on a treatment couch;
rotating a gantry coupled to a frame of the radiation treatment machine;
emitting cone-beam radiation from a radiation source coupled to the gantry;
transmitting at least a portion of the cone-beam radiation through said patient;
capturing first image projection data using a flat-panel kV imager coupled to the gantry, wherein capturing the first image projection data includes capturing at least a portion of the portion of the cone-beam radiation transmitted through said patient;
generating cone-beam computed tomography (CT) volumetric image data from the first image projection data;
repositioning the patient based on the cone-beam computed tomography (CT) volumetric image data, wherein repositioning the patient comprises moving said treatment couch prior to beginning the clinical treatment;
applying therapeutic radiation to a target volume using the treatment plan; and
capturing second image projection data using a flat-panel MV imager coupled to the gantry, wherein capturing the second image projection data includes capturing at least a portion of the therapeutic radiation applied to the target volume at non-uniformly spaced angles with respect to rotation of the gantry.

12. The method of claim 11, wherein capturing the second image projection data includes continuously rotating the gantry about the target volume while capturing the second image projection data at non-uniformly spaced angles with respect to rotation of the gantry.

13. The method of claim 12, wherein capturing the second image projection data at non-uniformly spaced angles with respect to rotation of the gantry comprises predetermining non-uniformly spaced angles with respect to rotation of the gantry.

14. A method to perform a clinical treatment, comprising:
receiving a treatment plan at a computer of a radiation treatment machine;
positioning a patient at an initial position on a treatment couch;
rotating a gantry coupled to a frame of the radiation treatment machine;
emitting cone-beam radiation from a radiation source coupled to the gantry;
transmitting at least a portion of the cone-beam radiation through said patient;
capturing first image projection data using a flat-panel kV imager coupled to the gantry;
generating cone-beam computed tomography (CT) volumetric image data from the first image projection data;
repositioning the patient based on the cone-beam computed tomography (CT) volumetric image data, wherein repositioning the patient comprises moving said treatment couch prior to beginning the clinical treatment;
applying therapeutic radiation to a target volume using the treatment plan;
capturing second image projection data using a flat-panel MV imager coupled to the gantry, wherein capturing the second image projection data includes capturing at least a portion of the therapeutic radiation applied to the target volume at non-uniformly spaced angles with respect to rotation of the gantry; and
changing the speed of rotation of the gantry during rotation of the gantry.

15. The method of claim 14, wherein capturing the second image projection data includes continuously rotating the gantry about the target volume (1) while capturing the second image projection data at non-uniformly spaced angles with respect to rotation of the gantry, and (2) while changing the speed of rotation of the gantry during rotation of the gantry.

16. The method of claim 15, wherein capturing the second image projection data at non-uniformly spaced angles with respect to rotation of the gantry comprises predetermining non-uniformly spaced angles with respect to rotation of the gantry.

17. The method as in one of claim 1, 3, 6, 9, 11 or 14, further comprising adjusting a therapeutic radiation source into a position to align the target volume with the therapeutic radiation.

18. The method of claim 17, wherein said capturing first image projection data captures the first image projection data at a rate of at least 5 frames per second.

19. The method of claim 17, wherein said capturing first image projection data captures the first image projection data at a rate of at least 15 frames per second.

20. The method of claim 17, further comprising storing the treatment plan and the first image projection data on said computer.

21. The method of claim 20, further comprising displaying said first image projection data on a monitor.

22. The method of claim 21, further comprising using said second image projection data to verify that the target volume is properly targeted.

23. The method of claim 20, further comprising displaying said second image projection data on a monitor.

24. The method of claim 23, further comprising using said second image projection data to verify that the target volume is properly targeted.

25. The method of claim 20, further comprising displaying said cone-beam computed tomography (CT) volumetric image data on a monitor.

26. The method of claim 25, further comprising using said second image projection data to verify that the target volume is properly targeted.

27. The method of claim 17, further comprising using said second image projection data to verify that the target volume is properly targeted.

* * * * *